(12) United States Patent
Zamyatin et al.

(10) Patent No.: US 7,359,478 B2
(45) Date of Patent: Apr. 15, 2008

(54) METHOD FOR RESTORING TRUNCATED HELICAL CONE-BEAM COMPUTED TOMOGRAPHY DATA

(75) Inventors: Aleksandr A. Zamyatin, Buffalo Grove, IL (US); Katsuyuki Taguchi, Buffalo Grove, IL (US); Michael D. Silver, Northbrook, IL (US)

(73) Assignees: Toshiba Medical Systems Corporation, Otawara-shi (JP); Kabushiki Kaisha Toshiba, Tokyo (JP)

( * ) Notice: Subject to any disclaimer, the term of this patent is extended or adjusted under 35 U.S.C. 154(b) by 355 days.

(21) Appl. No.: 10/990,464

(22) Filed: Nov. 18, 2004

(65) Prior Publication Data

US 2006/0104407 A1 May 18, 2006

(51) Int. Cl.
*A61B 6/03* (2006.01)
(52) U.S. Cl. .............................. 378/15; 378/4; 378/19; 378/901
(58) Field of Classification Search .................... 378/4, 378/15, 19, 901, 5
See application file for complete search history.

(56) References Cited

U.S. PATENT DOCUMENTS

| | | | | |
|---|---|---|---|---|
| 6,233,308 B1 * | 5/2001 | Hsieh | ........................ | 378/62 |
| 6,529,575 B1 * | 3/2003 | Hsieh | ........................ | 378/4 |
| 2004/0165695 A1 * | 8/2004 | Karimi et al. | ................ | 378/19 |
| 2006/0140335 A1 * | 6/2006 | Heuscher et al. | ............... | 378/4 |

OTHER PUBLICATIONS

Proksa et al., The n-PI-Method for Helical Cone-Beam CT, IEEE Transactions on Medical Imaging, vol. 19, No. 9, pp. 848-863, Sep. 2000.*
Lui et al., X-ray micro-CT with a displaced detector array: Application to helical cone-beam reconstruction, Med. Phys., 30, (10), pp. 2758-2761, Oct. 2003.*
Ge Wang, X-Ray Micro-CT With a Displaced Detector Array, Medical Physics, vol. 29, No. 7, Jul. 2002, pp. 1634-1636.
Vinson Liu, et al., X-Ray Micro-CT With a Displaced Detector Array: Application to Helical Cone-Beam Reconstruction, Medical Physics, vol. 30, No. 10, Oct. 2003, pp. 2758-2761.

* cited by examiner

*Primary Examiner*—Edward J. Glick
*Assistant Examiner*—John M Corbett
(74) *Attorney, Agent, or Firm*—Oblon, Spivak, McClelland, Maier & Neustadt, P.C.

(57) ABSTRACT

A method, system, and computer program product for compensating for the unavailability of projection data of a scanned object at a selected point, the selected point located outside a detection range of a detector. The method include the steps of obtaining projection data of the scanned object, and compensating for the unavailability of the projection data at the selected point based on the obtained projection data and coordinates of the selected point relative to the detector. The compensating step includes determining at least one complementary projection angle and coordinates of at least one complementary point based on a source projection angle and the coordinates of the selected point relative to the detector, and estimating the projection data value at the selected point based on the acquired projection data, the at least one complementary projection angle, and the coordinates of the at least one complementary point.

49 Claims, 18 Drawing Sheets

METHOD FOR RESTORING TRUNCATED HELICAL CONE-BEAM COMPUTED TOMOGRAPHY DATA

BACKGROUND OF THE INVENTION

Field of the Invention

The present invention is directed to the restoration of asymmetrically truncated imaging data. More precisely the present invention relates to methods for restoring truncated helical cone-beam computed tomography (CT) data when truncation occurred as a result of displacing the detector so that its field of view (FOV) fully covers an oversized object.

The present invention includes the use of various technologies referenced and described in the documents identified in the following LIST OF REFERENCES, which are cited throughout the specification by the corresponding reference number in brackets:

LIST OF REFERENCES

[1] P. E. Danielsson, P. Edholm, J. Eriksson and M. Seger, Towards exact 3D-reconstruction for helical cone-beam scanning of long objects. A new detector arrangement and a new completeness condition, *Proc. on Fully 3D Image Reconstruction in Radiology and Nuclear Med.*, 141-144, 1997.
[2] V. Liu, N. R. Lariviere, and G. Wang, X-ray micro-CT with a displaced detector array: Application to helical cone-beam reconstruction, *Med. Phys.*, 30(10), 2758-2761, 2003.
[3] D. L. Parker, Optimal short scan convolution reconstruction for fan beam CT, *Med. Phys.*, 9 (2), 254-257, 1982.
[4] M. D. Silver, A method for including redundant data in tomography, *Med. Phys.*, 27, 773-774, 2000.
[5] M. D. Silver, K. Taguchi, and K. S. Han, Field-of-view dependent helical pitch in multi-slice CT *Proc. of SPIE Med. Imag. Conf.* 4320, 839-850, 2001.
[6] K. Taguchi, B. S. Chiang and M. D. Silver, A new weighting scheme for cone-beam helical CT to reduce the image noise, *Phys. Med. Biol.*, 49, 2351-2364, 2004.
[7] K. C. Tam, S. Samarasekera, and F. Sauer, Exact cone-beam CT with a spiral scan, *Phys. Med. Biol.*, 43, 1015-1024, 1998.
[8] G. Wang, X-ray micro-CT with a displaced detector array, *Med. Phys.*, 29(7), 1634-1636, 2002.

The entire contents of the contents of each reference listed in the LIST OF REFERENCES are incorporated herein by reference.

DISCUSSION OF THE BACKGROUND

It is often necessary when attempting to obtain CT images of an object to have to displace the detector in order to increase the FOV. In the case of particularly large objects, the FOV may only achieve a partial coverage of the object. As a consequence, a certain level of truncation is often inevitable. One generally attempts, at the very least, to cover the object fully on one side. Since the quality of CT images is an essential aspect of the overall effectiveness of a CT device, it is desirable to devise methods restoring the truncated elements, which will improve the quality of the CT images.

FIG. 1 illustrates a typical ray trajectory with fan beam geometry. The ray emanates from a ray source, passes through an object to be scanned (which is fully covered by the FOV in this particular instance) and finally reaches the physical ray detector. More precisely, the ray source, denoted by $\alpha(\beta)$, is located along the broken-line circle at angular position $\beta$ with respect to the $x_I$-axis. Angle $\beta$ is called the projection angle. Both fan angle $\gamma$ and projection angle $\beta$ are directed counterclockwise. The detector has an angular range of $2\gamma_{max}$.

Cone-beam data are obtained using multi-slice or other area detector and is related to the cone-beam transform function $g(\beta,\Theta)$, where $\Theta$ represents the direction of the ray from the source $\alpha(\beta)$. (In the case of FIG. 1, $\Theta=\gamma$.) The cone-beam transform function is the line integral along the ray emanating from the source $\alpha(\beta)$ in the direction prescribed by $\Theta$. The cone-beam data, also called "projection data," are denoted by $PD(\beta,\Theta_D)$, where $\Theta_D=(u, v)$ represents the direction of the ray expressed in local detector coordinates. Note that local detector coordinates (u, v) are always considered projected at the isocenter.

It is important to note that the relation between $g(\beta,\Theta)$ and $PD(\beta,\Theta_D)$ is determined by the geometry of the detector. Moreover, detectors can have a variety of geometries. The equi-angular cylindrical detector and equi-spaced flat detector geometries are among the most common ones. Others possible geometries include non equi-spaced, spherical, tilted, rotated, and PI-masked.

FIG. 2 illustrates the equi-angular cylindrical detector geometry, a situation more complex than that represented in FIG. 1. In this case, $\Theta=(\gamma,\alpha)$, where $\gamma$ and $\alpha$ are, respectively, the fan and cone angles. Naturally, it is possible to use cylindrical rather than spherical coordinates, i.e., one could use $\Theta=(\gamma,z)$, where z takes values along a local axis collinear with the global Z axis seen in FIG. 2. For the equi-angular cylindrical detector, the local detector coordinates (u, v) are related to the local spherical coordinates ($\gamma$, $\alpha$) by the equations: $u=R\gamma$, $v=R \tan \alpha$.

FIG. 3 illustrates the equi-spaced flat detector geometry, another possible situation. Observe that the only difference is the local detector system of coordinates. The ray itself, the source and passage through the object are unchanged. For the equi-spaced flat detector, the local detector coordinates (u, v) are related to the local spherical coordinates ($\gamma$, $\alpha$) by the equations: $u=R \tan \gamma$, $v=R \tan \alpha$. In the case of FIG. 2 and FIG. 3, the source trajectory is helical. The trajectory can thus be expressed as $\alpha(\beta)=(R \cos \beta, R \sin \beta, \beta H/2\pi)$, wherein R and H respectively denote the radius and pitch of the helix. Note also that the "equi-spaced" and "equi-angular" descriptors pertain exclusively to the fan angle.

FIG. 4 illustrates asymmetrical data truncation. When a detector is displaced so that its FOV fully covers on one side an object or patient too large to be fully covered, a portion of the object or patient on the other side will not be scanned and data truncation will therefore occur. Two objects are shown in FIG. 4. The small one, represented by the solid circle, is fully covered and the large one, represented by the dashed circle, cannot fully be covered and leads to asymmetric truncation.

To address the problems associated with larger objects, Ge Wang [8] proposed to increase the diameter of the FOV by displacing the detector array by an amount not exceeding 50% of the detector range and formulated a weighting scheme for artifact-free reconstruction. This idea was originally proposed for fan beam reconstruction and later generalized to two-dimensional detectors with helical geometry [2]. In order to compensate for missing data, the fan beam weighting function was constructed to assign more weight to the asymmetric part of the detector. However, even though such an idea was applied to helical cone-beam geometry, no new developments to take into account the cone angle with regard to the weighting function are known. Moreover, the method of Wang cannot be used with short-scan reconstruction algorithms since it requires the entire revolution of data.

The idea of redundancy is known in the context of fan beam data, wherein it has previously been investigated. In one study, the back-projection range is reduced to a "minimum complete data set" [3]. In other studies, a flexible helical pitch-dependent back-projection range is allowed [4,5]. Other applications of complementary fan beam rays include so-called "quarter offset" techniques.

It is possible to compensate fan beam data truncation using complementary data. However, extending this idea to helical cone-beam data is not trivial by any means.

SUMMARY OF THE INVENTION

Accordingly, to overcome the problems of the related art, the present invention provides a method, system, and computer program product for tomographic reconstruction using asymmetrically truncated cone-beam or fan-beam data of a scanned object. According to the present invention, the principle of tomographic reconstruction when projection data is asymmetrically truncated includes exploiting the redundancy of available data to compensate missing data on one side of the detector using measured data on the other side at opposite projection angles. One way to do this is to generate complementary ray-sums and thereby restore truncated data. Another way is to use asymmetric weight function to weight measured data in the weighting step of tomographic reconstruction. Such a weight function takes advantage of the redundancy of asymmetrically measured data without generating missing rays.

Accordingly, there is provided a method, system, and computer program product for tomographic reconstruction using asymmetrically truncated cone-beam or fan-beam data of a scanned object, comprising a compensation unit and an image reconstruction unit.

According to an aspect of the present invention, there is provided a method, system and computer program product for compensating for the unavailability of projection data of a scanned object at a selected point, the selected point located outside a detection range of a detector, comprising: (1) obtaining projection data of the scanned object; and (2) compensating for the unavailability of the projection data at said selected point based on the obtained projection data and coordinates of the selected point relative to the detector.

According to another aspect of the present invention, there is provided a method, system, and computer program product for estimating a projection data value of a scanned object at a selected point, the selected point located outside a detection range of a detector or within a predetermined region of the detector, comprising: (1) obtaining projection data of the scanned object; (2) determining at least one complementary projection angle and coordinates of at least one complementary point based on a source projection angle and coordinates of the selected point relative to the detector; and (3) estimating the projection data value at the selected point based on the obtained projection data, the at least one complementary projection angle, and the coordinates of the at least one complementary point.

Accordingly, there is provided a method, system, and computer program product for tomographic reconstruction using asymmetrically truncated cone-beam or fan-beam data of a scanned object, comprising: (1) obtaining projection data of the scanned object; (2) weighting data to compensate truncation on one side of the detector using measured data on the other side; and (3) image reconstruction from weighted data using arbitrary reconstruction method, appropriate for a given geometry.

Moreover, there is provided a computed tomography (CT) system to compensate for the unavailability of projection data of a scanned object at a selected point, the selected point located outside a detection range of a detector, comprising: (1) an X-ray source configured to project X-rays at a scanned object; (2) an asymmetric CT detector configured to detect said X-rays and to generate helical cone-beam CT projection data of the scanned object; and (3) a compensating processor configured to compensate for the unavailability of the projection data at said selected point based on the generated projection data and coordinates of the selected point relative to the CT detector.

Moreover, according to an aspect of the present invention, the use of redundant cone-beam data is extended to helical cone-beam geometry.

Embodiments of the present invention include means to restore asymmetrically truncated data that can potentially be used with any reconstruction algorithm, e.g., short-scan, full-scan, or over-scan. More specifically, reconstruction algorithms include direct fan or cone beam reconstruction, fan-to-parallel or cone-to-parallel rebinning algorithms, and a wedge algorithm can be used.

Embodiments of the present invention include means to restore asymmetrically truncated data that can potentially be used with any type of detector geometry, including equi-spaced, equi-angular, non equi-spaced, flat, cylindrical, spherical, tilted, rotated, and PI-masked.

According to another aspect of the present invention, a Tam window concept [1,7], formed by projections of adjacent helix turns onto the detector plane, is used.

Other methods, systems, and computer program products of the present invention will become apparent to one of ordinary skill in the art upon examination of the following drawings and detailed description of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 4:
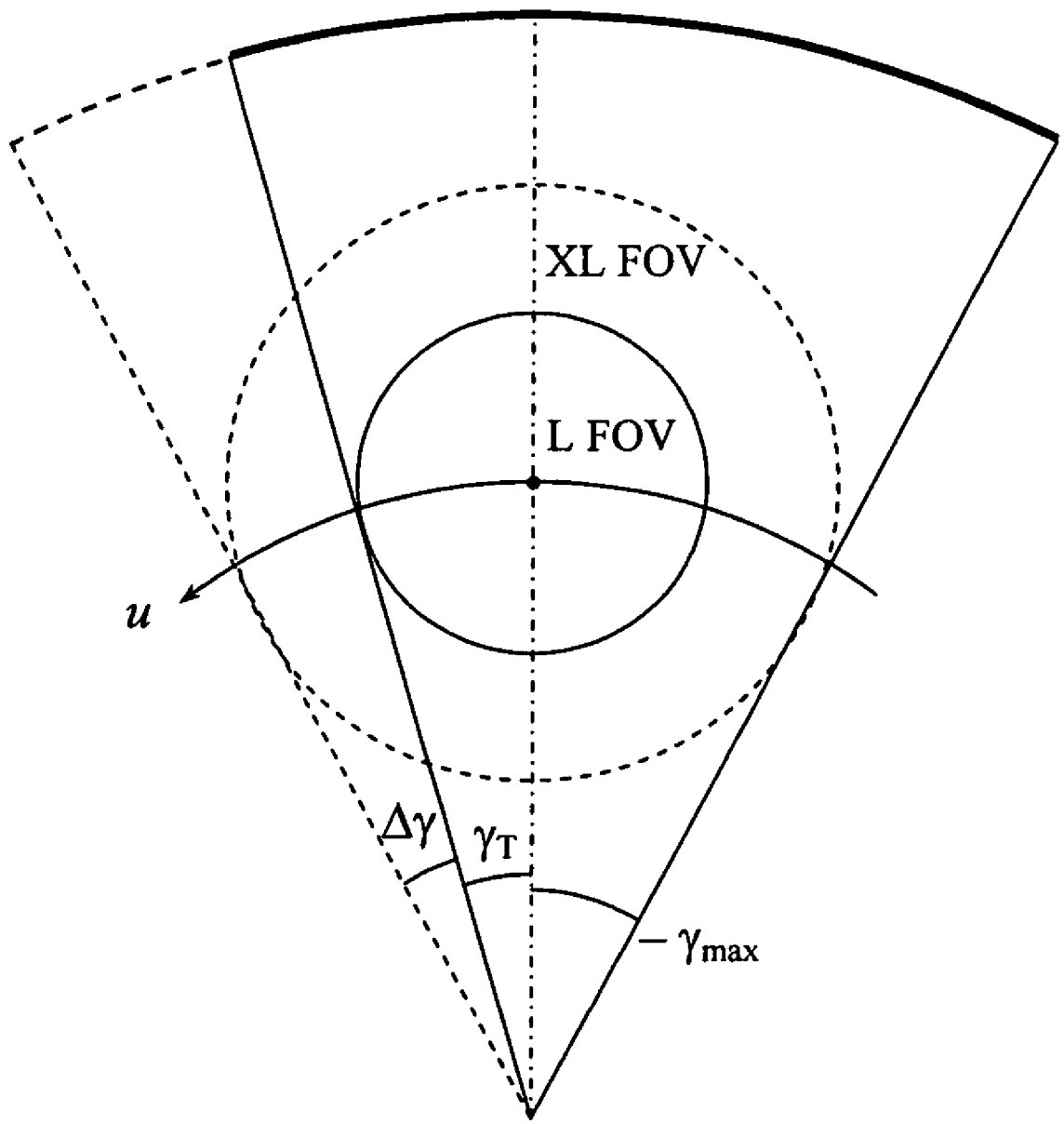
FIG. 4 illustrates an example of asymmetric truncation.
Figure 5:
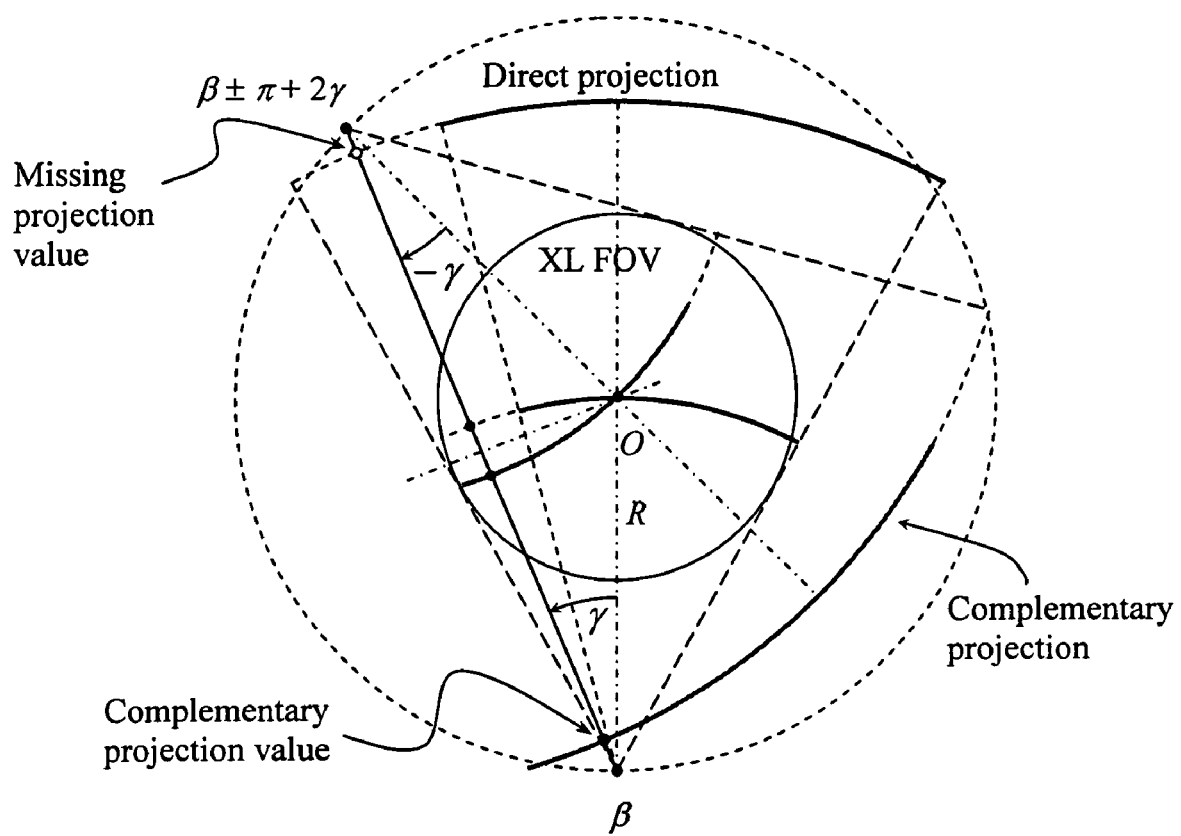
FIG. 5 illustrates the relation between direct and complementary projections.

FIG. 5 illustrates the notion of a complementary ray. A fan beam ray $(\beta,\gamma)$ has a complementary ray $(\beta+\pi+2\gamma,-\gamma)$ such that $g(\beta,\gamma)=g(\beta+\pi+2\gamma, -\gamma)$. Suppose that fan beam data are available and that the entire FOV that would be needed to fully cover the object, $g(\beta,\gamma)$, $\beta>0$, $-\gamma_{max} \leq \gamma \leq \gamma_{max}$, exceeds the detector angular range. For instance, there might be a truncation area corresponding to $\gamma_T \leq \gamma \leq \gamma_{max}$, $\gamma_T > 0$ while the data are known for $-\gamma_{max} \leq \gamma \leq \gamma_T$. See, e.g., FIG. 4. It follows that for a truncated ray $(\beta_0,\gamma_0)$ with $\gamma_T \leq \gamma_0 \leq \gamma_{max}$, the complementary ray $(\beta_0^C, \gamma_0^C) = (\beta_0+\pi+2\gamma_0, -\gamma_0)$ is known since $-\gamma_{max} \leq \gamma_0^C \leq -\gamma_T$.

The projection angles $\beta \pm \pi + 2\gamma$ are called complementary to the ray $(\beta,\gamma)$. For a circular geometry, it does not matter from a purely geometrical standpoint which complementary projection is used since $g(\beta+\pi+2\gamma,-\gamma)=g(\beta-\pi+2\gamma,-\gamma)$. However, it turns out in practice that using a weighted sum of both complementary projections, e.g., $g(\beta,\gamma)=w_1 g(\beta+\pi+2\gamma,-\gamma)+w_2 g(\beta-\pi+2\gamma,-\gamma)$, where $w_1$, $w_2>0$ and $w_1+w_2=1$, leads to an improved image quality when reconstructing from noisy data.

The above analysis can be extended to helical cone-beam data. Generalizing from the above, a cone-beam ray $(\beta,\gamma,\alpha)$ leads to complementary angles $\beta \pm \pi + 2\gamma$ such that $g(\beta,\gamma,\alpha)=g(\beta+\pi+2\gamma,-\gamma,\alpha)$ and $g(\beta+\pi+2\gamma,-\gamma,\alpha)=g(\beta-\pi+2\gamma,-\gamma,\alpha)$. However, whereas such a simple extension may provide a relatively good approximation for circular trajectories, it fails for helical geometry, wherein new developments are needed. To that end, let the projection corresponding to a source angular position $\beta$ be called the direct projection and let a projection corresponding to a complementary source angular position be called a complementary projection.

Figure 6:
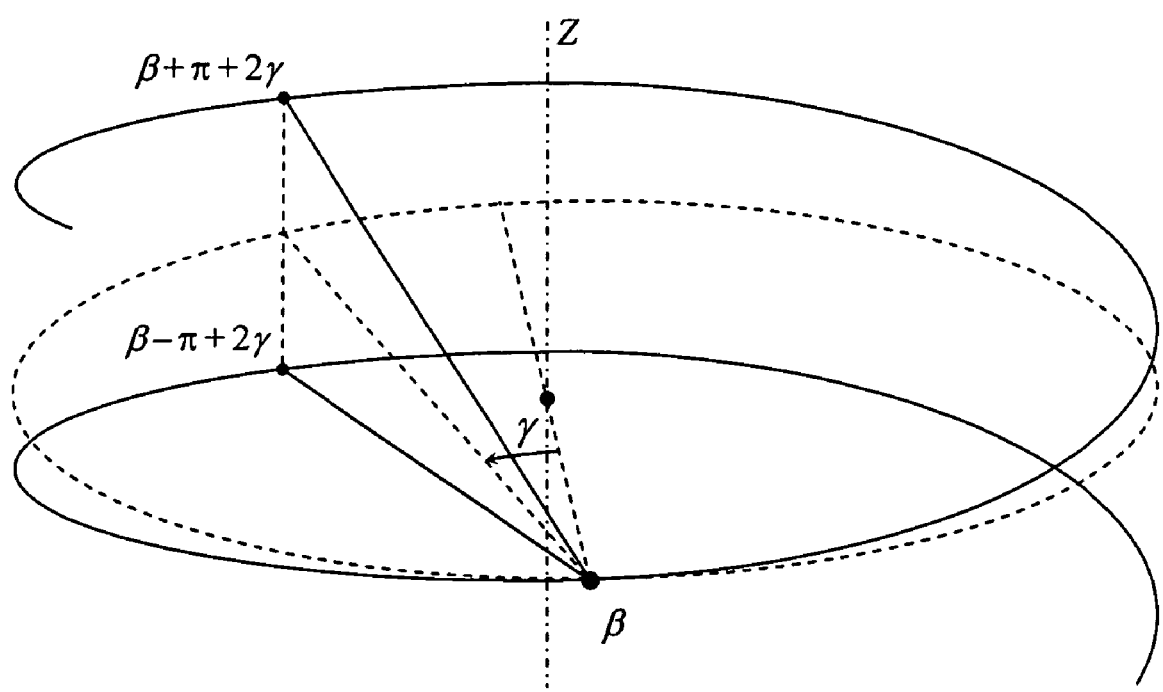
FIG. 6 illustrates the positions of complementary sources on a helix.

FIG. 6 illustrates the two complementary projections that can be found in helical geometry. One is above and the other is below the direct projection. Define further the complementary projection corresponding to $\beta+\pi+2\gamma$ to be the top complementary projection and the complementary projection corresponding to $\beta-\pi+2\gamma$ to be the bottom complementary projection. An important component of the present method is determining the coordinates of the complementary projections, which are to be used to restore the asymmetrically truncated data.

It is important to note at this point that whereas aspects of the present invention will now be discussed partly in terms of the equi-space and equi-angular geometries, it is by no means limited to these types of detectors, and could be applied to any other type of detector geometry, including non equi-spaced, spherical, tilted, rotated, and PI-masked.

The coordinates of the top and bottom complementary projections will now be derived. To emphasize that the scope of the invention is not limited to such common detector geometries as the equi-angular curved detector and equi-spaced flat detector, spherical and cylindrical coordinates will first be derived. These could be used with arbitrary geometries being detector-free coordinates. Particular sets of coordinates for the two common geometries mentioned above will be derived below.

Figure 7:
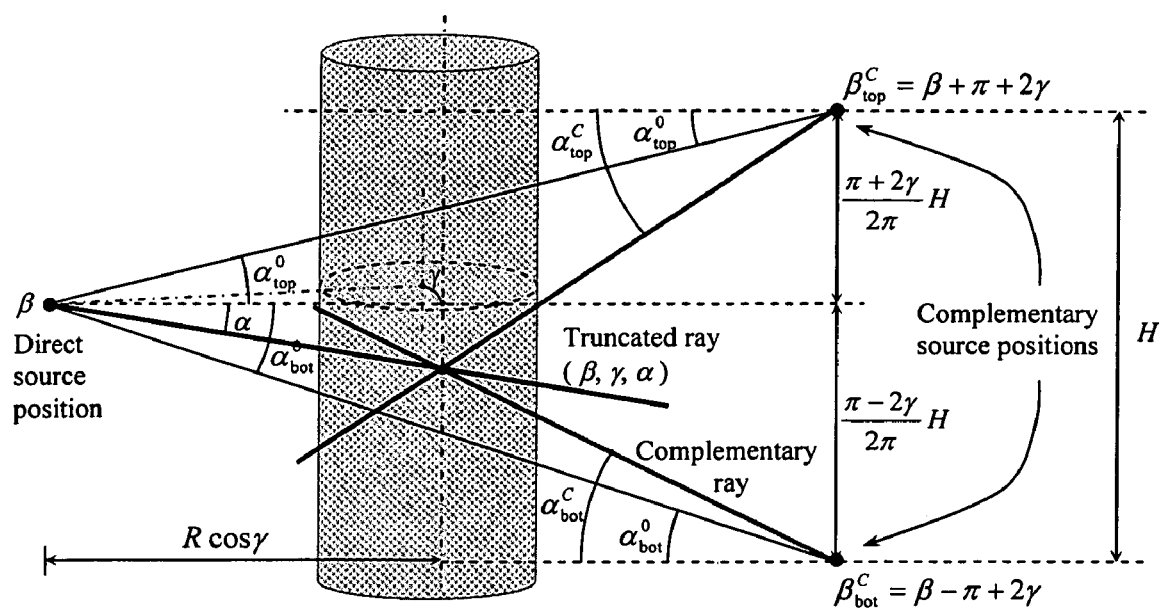
FIG. 7 illustrates complementary cone-beam rays and sources.

FIG. 7 illustrates two specific cone angles, $\alpha_{top}^0$ and $\alpha_{bot}^0$, for which exact complementary rays exist. Expressed in spherical coordinates, these cone angles are such that $g(\beta,\gamma,\alpha_{top}^0)=g(\beta+\pi+2\gamma,-\gamma,-\alpha_{top}^0)$ and $g(\beta,\gamma,\alpha_{bot}^0)=g(\beta-\pi+2\gamma,-\gamma,-\alpha_{bot}^0)$. The angles $\alpha_{top}^0$ and $\alpha_{bot}^0$ define the common rays with upper and lower projections and can be expressed as $$\alpha_{top}^0 = \tan^{-1}\left(\frac{H}{4\pi R}\frac{\pi+2\gamma}{\cos\gamma}\right) \text{ and } \alpha_{bot}^0 = -\tan^{-1}\left(\frac{H}{4\pi R}\frac{\pi-2\gamma}{\cos\gamma}\right).$$

For other cone angle values, no exact complementary rays exist. In such cases, it will be necessary for the truncated data $g(\beta,\gamma,\alpha)$ to be interpolated between two close rays $g(\beta_{top}^C,-\gamma,\alpha_{top}^C)$ and $g(\beta_{bot}^C,-\gamma,\alpha_{bot}^C)$, as shown in FIG. 7.

Figure 8:
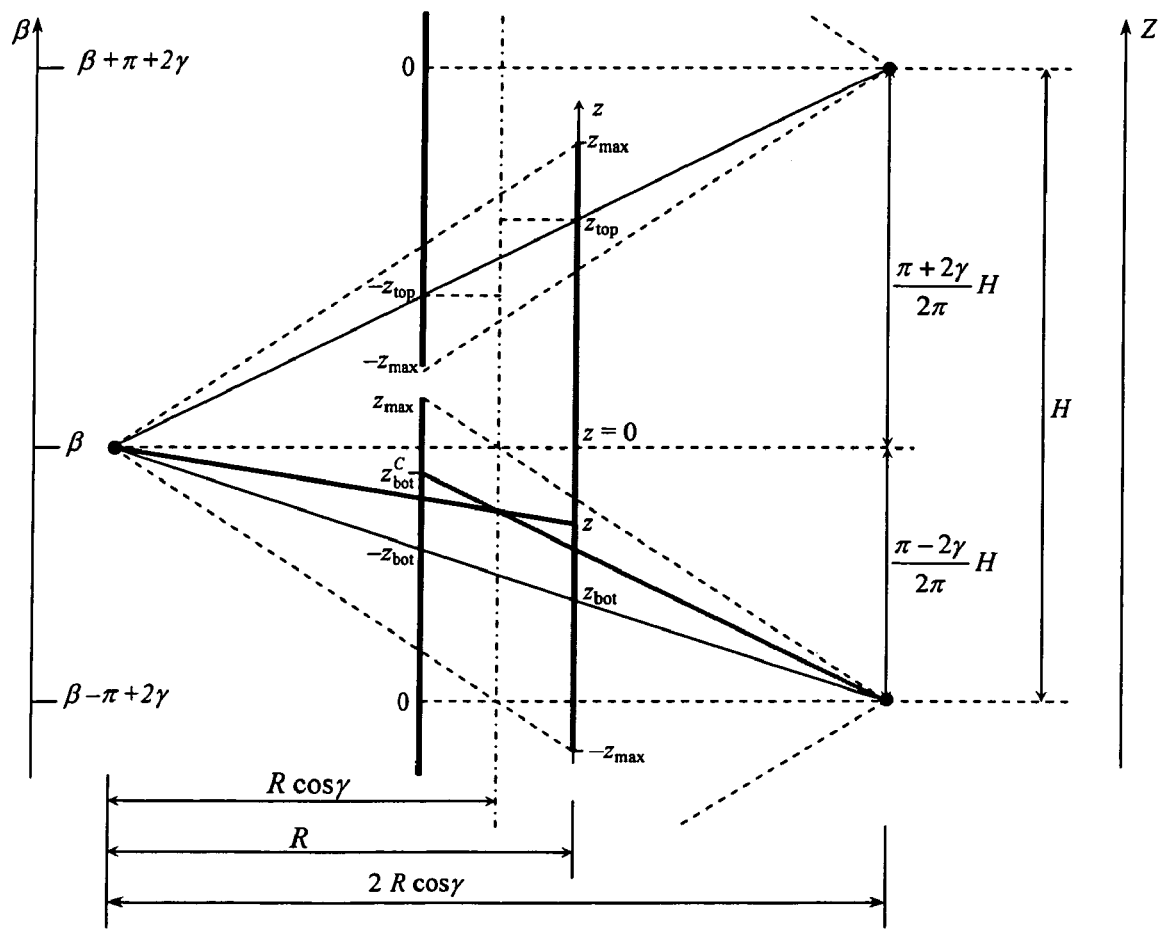
FIG. 8 illustrates detector coordinates for complementary cone-beam rays and sources.

FIG. 8 illustrates the complementary coordinates along axes collinear with the global Z axis. In cylindrical coordinates, a direct projection $g(\beta,\gamma,z)$ has common ray with each of the complementary projections $g(\beta,\gamma,z_{top})=g(\beta+\pi+2\gamma,-\gamma,-z_{top})$ and $g(\beta,\gamma,z_{bot})=g(\beta+\pi+2\gamma,-\gamma,-z_{bot})$. Moreover, it can be derived from FIG. 8 by similarity of triangles that $$z_{top} = \frac{H}{4\pi}\frac{\pi+2\gamma}{\cos\gamma} \text{ and } z_{bot} = -\frac{H}{4\pi}\frac{\pi-2\gamma}{\cos\gamma}.$$

It is possible to use this to derive the complementary coordinates for an arbitrary ray $(\beta,\gamma,z)$. To that end, respectively denote the top and bottom complementary projections by $(\beta_{top}^C, \gamma_{top}^C, \alpha_{top}^C)$ and $(\beta_{bot}^C, \gamma_{bot}^C, \alpha_{bot}^C)$. Complementary rays are chosen so that they intersect the direct ray at the midpoint between the focal spots. As a result, the distance between the intersection of the complementary ray with the focal plane and that of the direct ray with the focal plane is the same for both complementary rays. For example, for the bottom complementary ray, these distances are equal and expressed as $z_{bot}^C - (-z_{bot}) = z - z_{bot}$. As a consequence, $z_{top}^C = z - 2z_{top}$ and $z_{bot}^C = z - 2z_{bot}$, so that the top complementary projection is $$(\beta_{top}^C, \gamma_{top}^C, z_{top}^C) = \left(\beta+\pi+2\gamma, -\gamma, z-\frac{H}{2\pi}\frac{\pi+2\gamma}{\cos\gamma}\right)$$

and the bottom complementary projection is $$(\beta_{bot}^C, \gamma_{bot}^C, z_{bot}^C) = \left(\beta-\pi+2\gamma, -\gamma, z+\frac{H}{2\pi}\frac{\pi-2\gamma}{\cos\gamma}\right).$$

Naturally, the manner in which the complementary rays are chosen could vary. Other mechanisms could be used by those of ordinary skill in the art, which would result in slightly modified expressions for the complementary rays, but the principle remains unchanged.

Figure 1:
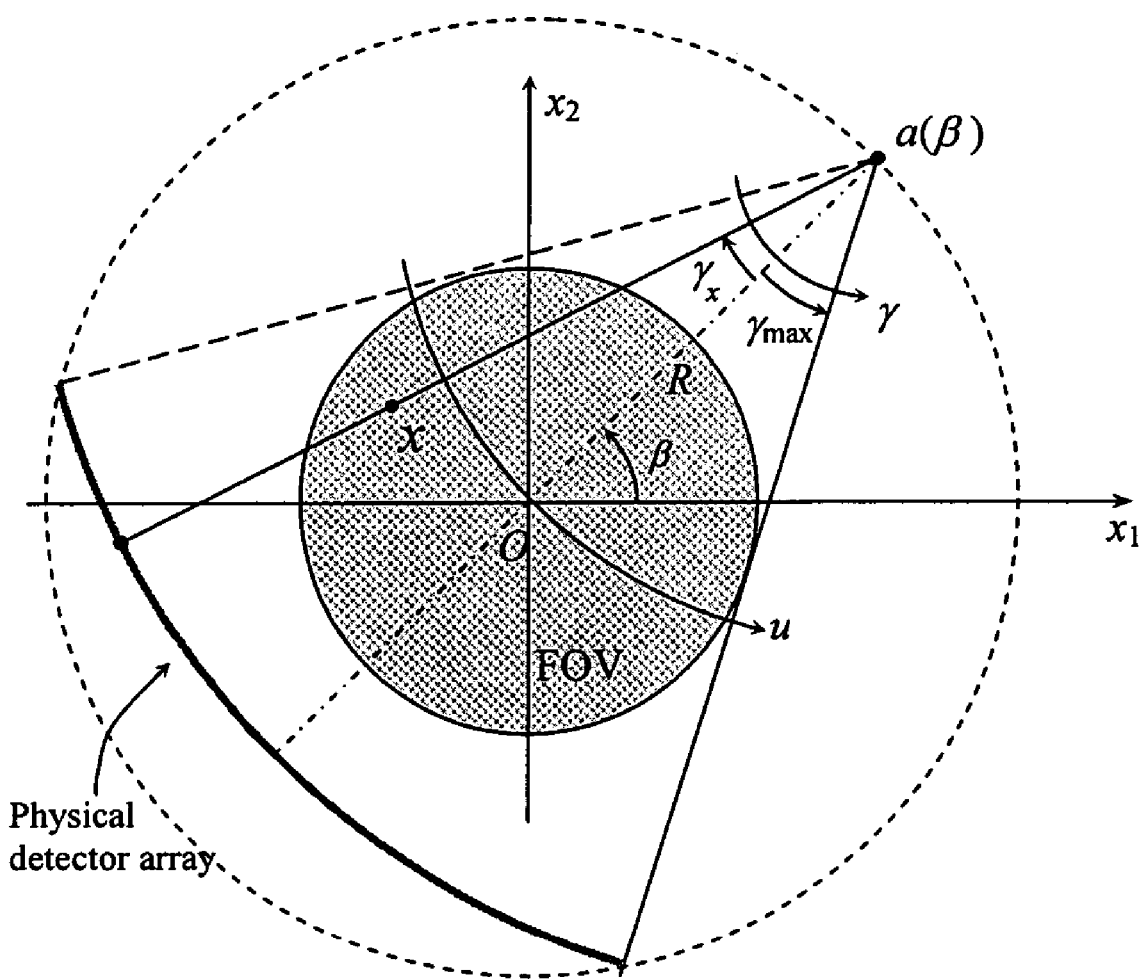
FIG. 1 illustrates a ray with fan beam geometry.
Figure 2:
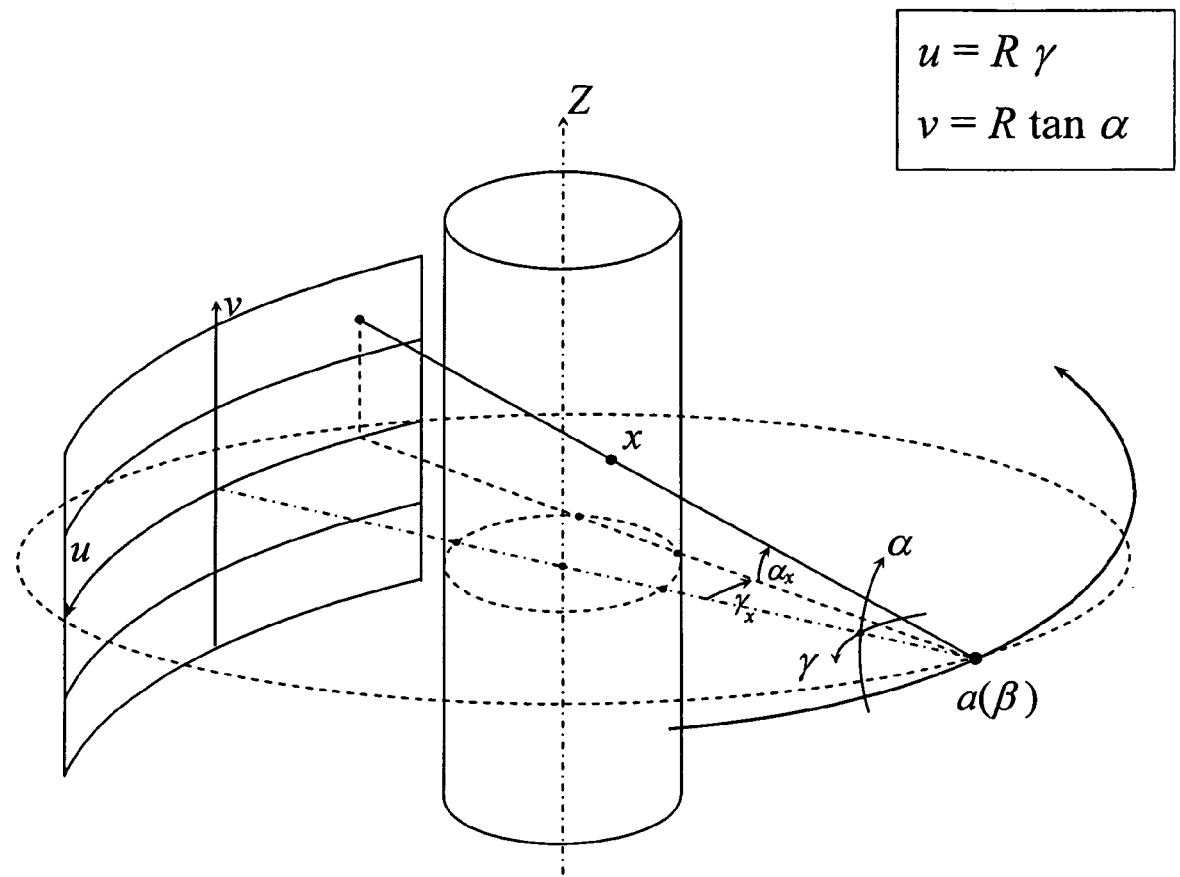
FIG. 2 illustrates a ray with helical source trajectory and equi-angular curved detector geometry.
Figure 3:
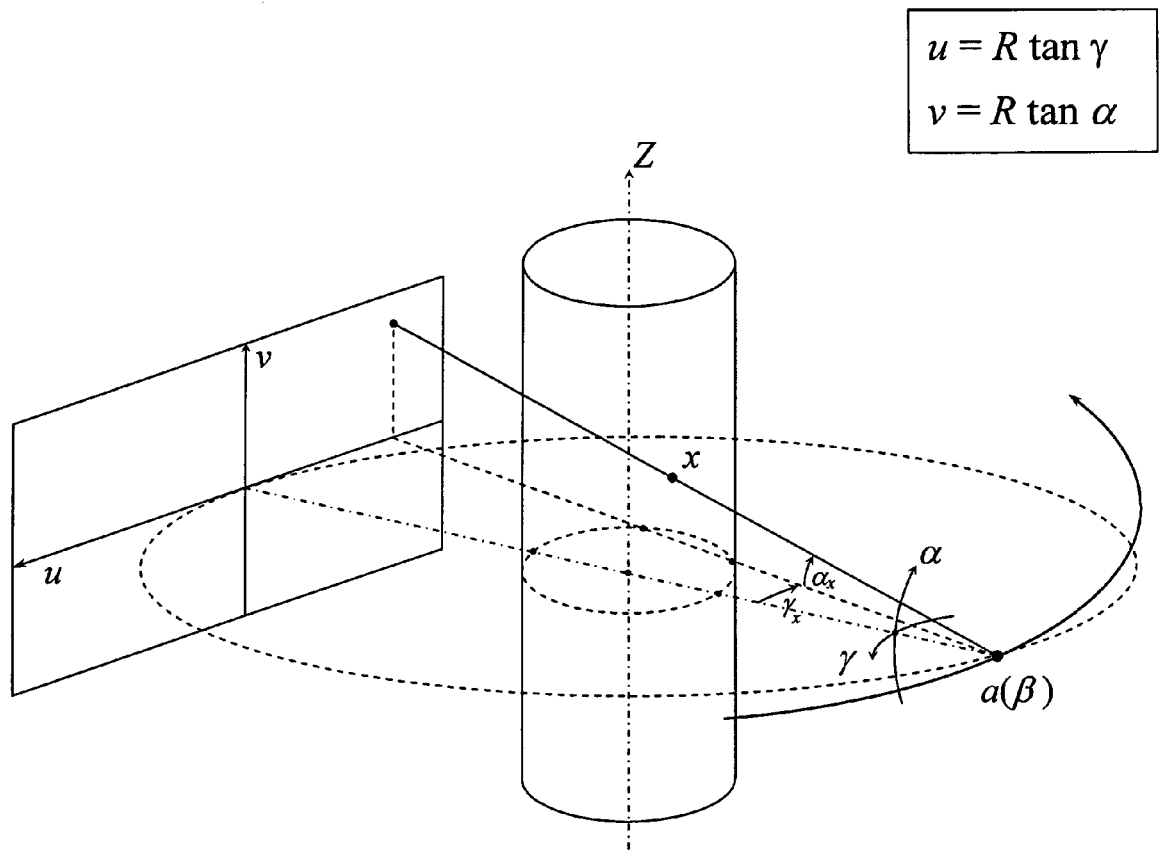
FIG. 3 illustrates a ray with helical source trajectory and equi-spaced flat detector geometry.

General expressions such as these, expressed in spherical or cylindrical coordinates, can lead to detector-specific expressions for complementary ray coordinates. In the case of an equi-angular curved detector, whose curvature follows a circular arc around the position of the source (see FIG. 2) and which is considered projected at the isocenter (so that the v and z axes coincide), (γ,z) and (u,v) are related by u=Rγ, where R is the radius, and v=z. Therefore, for an equi-angular detector, the top complementary projection is $$(\beta_{top}^C, u_{top}^C, v_{top}^C) = \left(\beta + \pi + 2\gamma, -u, v - \frac{H}{2\pi}\frac{\pi + 2u/R}{\cos(u/R)}\right)$$

and the bottom complementary projection is $(\beta_{bot}^C, u_{bot}^C, v_{bot}^C) = \left(\beta - \pi + 2\gamma, -u, v + \frac{H}{2\pi}\frac{\pi - 2u/R}{\cos(u/R)}\right)$.

Figure 9:
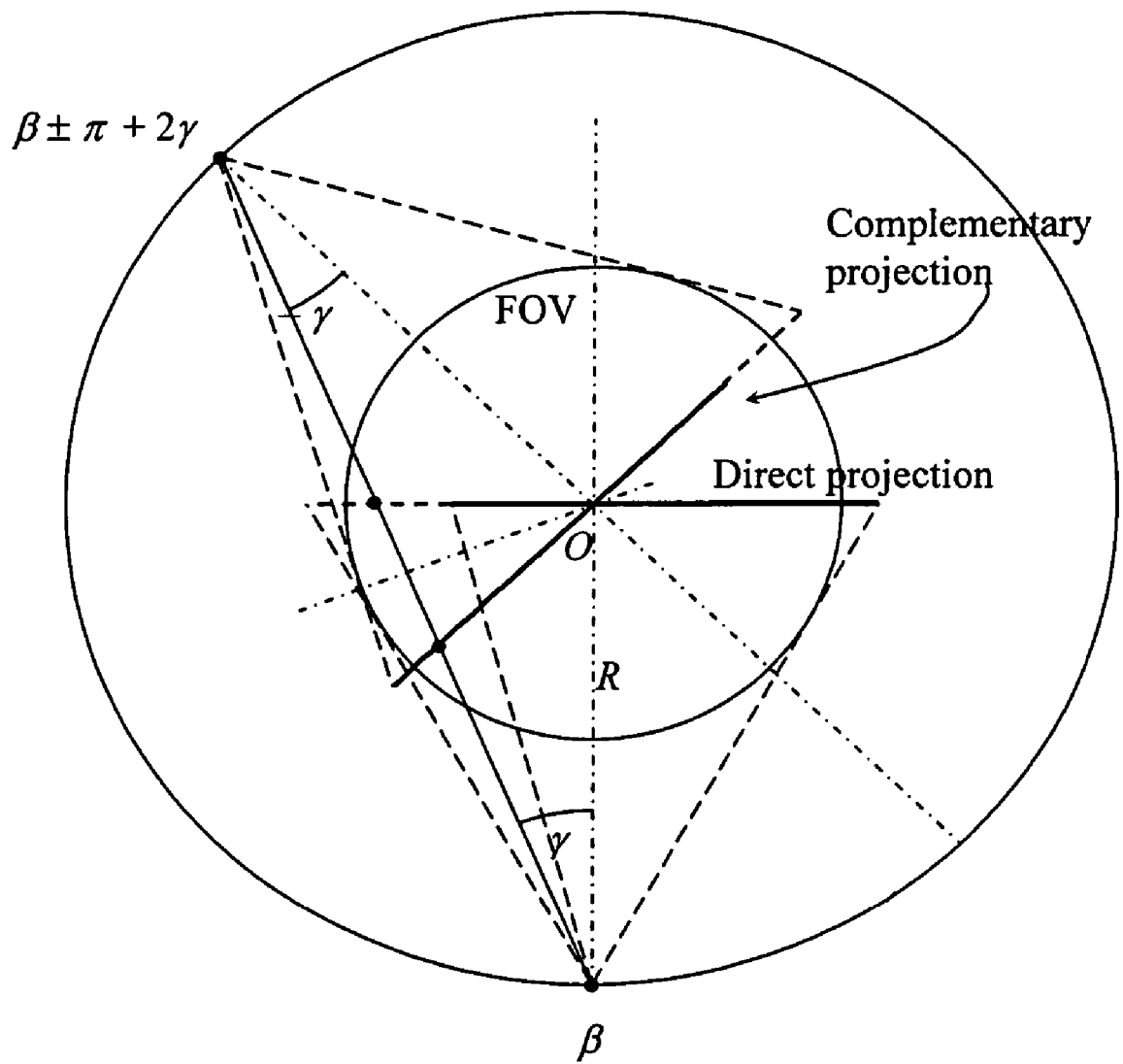
FIG. 9 illustrates direct and complementary projections with a flat detector and fan beam geometry.

In the case of an equi-space flat detector, (γ,z) and (u, v) are related by u=R tan γ and v=z. It is possible to write, by similarity of triangles, and considering that the distance between the focal spot and the detector is R/cos γ (see FIG. 9), that $$\frac{z_{top}}{R/\cos\gamma} = \frac{((\pi + 2\gamma)/2\pi)H}{2R\cos\gamma}.$$

(A similar observation can be made for $z_{bot}$.) As a result, $$z_{top} = \frac{H}{4\pi}\frac{\pi + 2\gamma}{\cos^2\gamma} \text{ and } z_{bot} = \frac{H}{4\pi}\frac{\pi - 2\gamma}{\cos^2\gamma},$$

so that the top complementary projection is $$(\beta_{top}^C, u_{top}^C, v_{top}^C) = \left(\beta + \pi + 2\gamma, -u, v - \frac{\pi + 2\tan^{-1}(u/R)}{2\pi}\frac{H(u^2 + R^2)}{R^2}\right)$$

whereas the bottom one $$(\beta_{bot}^C, u_{bot}^C, v_{bot}^C) = \left(\beta - \pi + 2\gamma, -u, v + \frac{\pi - 2\tan^{-1}(u/R)}{2\pi}\frac{H(u^2 + R^2)}{R^2}\right).$$

The coordinates of the complementary projections, whatever their representation, will be used to restore the truncated data. However, the projection data are given in discrete coordinates (β(l),u(k),v(n)), where l=1, ..., L, k=1, ..., K, and n=1, ..., N, and as a result the derived complementary coordinates $(\beta^C, u^C, v^C)$ may not coincide with actual projection data points. The invention comprises means to confront this issue by interpolating the projections thereby identified to obtain restored truncated data that are much more accurate in the case of helical cone-beam CT.

There are several ways to perform interpolation for a ray $(\beta_{top}^C, u_{top}^C, v_{top}^C)$. A sample of possible interpolation techniques will now be provided. However, it should be noted that the invention is not limited to any particular interpolation technique. Many possible interpolation techniques would come to mind to people of ordinary skill in the art and they could easily be integrated or adapted to the present invention.

As a first example, one could use three-dimensional nearest-neighbor interpolation. This consists of using as complementary data a single data point, one which is nearest to $(\beta_{top}^C, u_{top}^C, v_{top}^C)$. This is the simplest and the most computationally effective interpolation approach. However, it yields the worst image quality among all linear interpolation methods.

Another possibility is one-dimensional linear interpolation, which occurs along a single direction. This can be used when the sample grid is sparser along that direction (e.g., along v).

Similarly, two-dimensional linear interpolation, wherein nearest neighbor interpolation is performed along one direction, and plain one-dimensional linear interpolation along the other directions, can be used when the sample grid is denser in one direction (e.g., along u) or when interpolation in one direction, like β, is harder to implement.

Finally, three-dimensional linear interpolation can also be used. This is, as one might expect, the most accurate interpolation method. However, it is also the most computationally demanding. In this case, complementary ray $(\beta_{top}^C, u_{top}^C, v_{top}^C)$ is interpolated using 8 adjacent data points.

It is also possible to perform double interpolation. That is, interpolation between two complementary projections. One can perform double interpolation either through a reduction to single interpolation, or, alternatively, through the feathering of two single interpolations, which yields smoother results. The restored truncated data thereby obtained are furthermore feathered with non-truncated data to ensure a smooth transition. Details are provided below.

Figure 10:
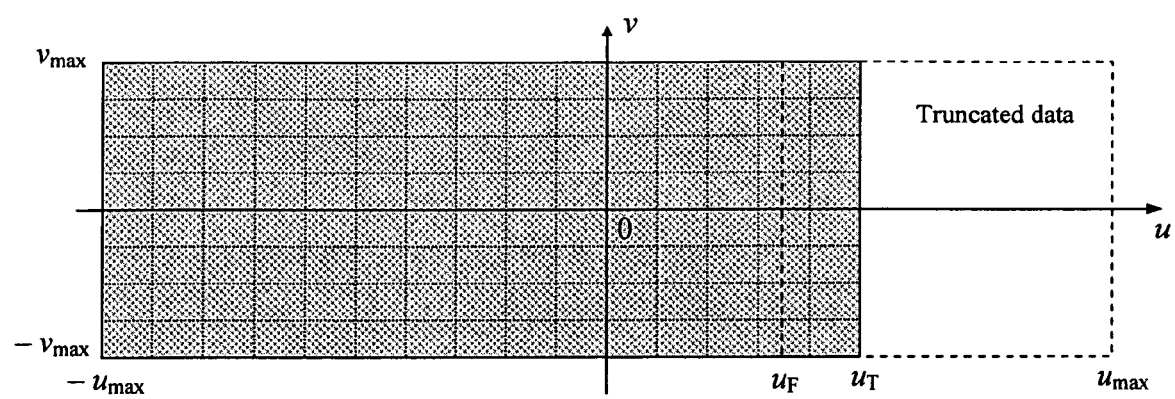
FIG. 10 illustrates a detector along with its coordinates and both truncated and un-truncated areas.

FIG. 10 illustrates the detector coordinates (u,v) used forthwith. The total detector area which would be needed to fully cover the scanned object is given by those coordinates (u,v) such that $-u_{max} \leq u \leq u_{max}$ and $-v_{max} \leq v \leq v_{max}$. Since the physical detector has to be displaced to fully cover the scanned object on one side, data on the other side is truncated. This truncated detector area consists of those coordinates (u,v) such that $u_T \leq u \leq u_{max}$, $u_T > 0$.

Suppose without loss of generality that the projection range is $0 \leq \beta \leq B$. It must then be the case that $\beta_{top}^C = \beta + \pi + 2\gamma \leq B$ and $\beta_{bot}^C = \beta - \pi + 2\gamma \geq 0$. Otherwise, data would have been obtained outside the projection range. Here, γ changes from $\gamma_0$ to $\gamma_{max}$. As a consequence, $\beta \leq B - \pi - 2\gamma$ and $\beta \geq \pi - 2\gamma$, so that no top complementary projection exists if $\beta > B - \pi - 2\gamma$ and no bottom complementary projection exists if $\beta < \pi - 2\gamma$.

Figure 11:
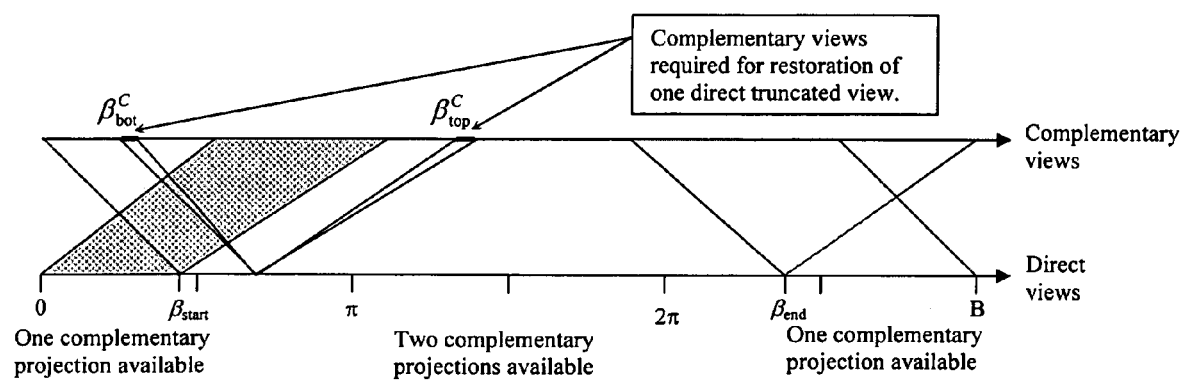
FIG. 11 illustrates a projection range.

FIG. 11 illustrates for a projection range of B=3π the region where both projections are available. This region is delimited by projection angles $\beta_{start}(\gamma) = \pi - 2\gamma$ and $\beta_{end}(\gamma) = B - \pi - 2\gamma$, expressions which can also be expressed more conveniently as $\beta_{start} = \max_\gamma \beta_{start}(\gamma) = \pi - 2\gamma_T$ and $\beta_{end} = \min_\gamma \beta_{end}(\gamma) = B - \pi - 2\gamma_{max}$. The complementary range for a single direct ray is $\Delta\beta^C = 2\Delta\gamma$, where $\Delta\gamma = \gamma_{max} - \gamma_T$ is the angular range of truncation.

In the case of helical geometry, there is some vertical shift between projections complementary to one another. As a result, a complementary projection may not cover the direct projection from top to bottom. It is therefore better, when attempting to restore truncated data, to use both complementary projections, whenever they are available.

Figure 12:
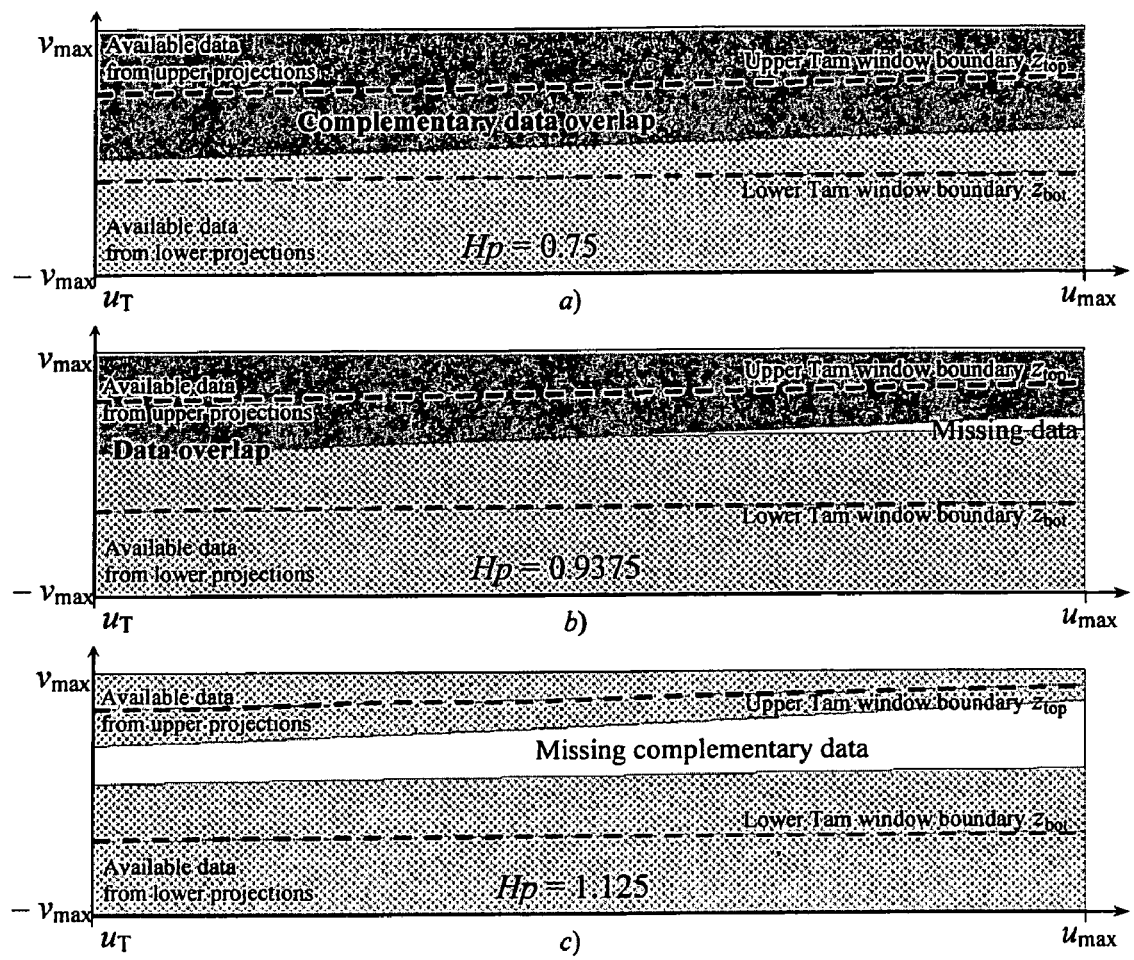
FIG. 12 illustrates, for various helical pitches, the data overlap or missing data regions.

FIG. 12 illustrates different data coverage situations, corresponding to different helical pitches. If the helical pitch is larger than the width of the detector, then complementary projections do not cover the middle part of the direct projection (see FIG. 12c). In such a case, when there are no complementary data available for the middle part, some extrapolation is required. Smaller helical pitches, on the other hand, lead to complementary projections that overlap the middle part of the direct projection (see FIG. 12a). This leads to more accurate interpolation. For some intermediate values of helical pitch, both cases can simultaneously occur (see FIG. 12b).

The invention can restore the data by extrapolation when complementary projections are not available and by interpolation when one or more complementary projections are available.

Figure 13:
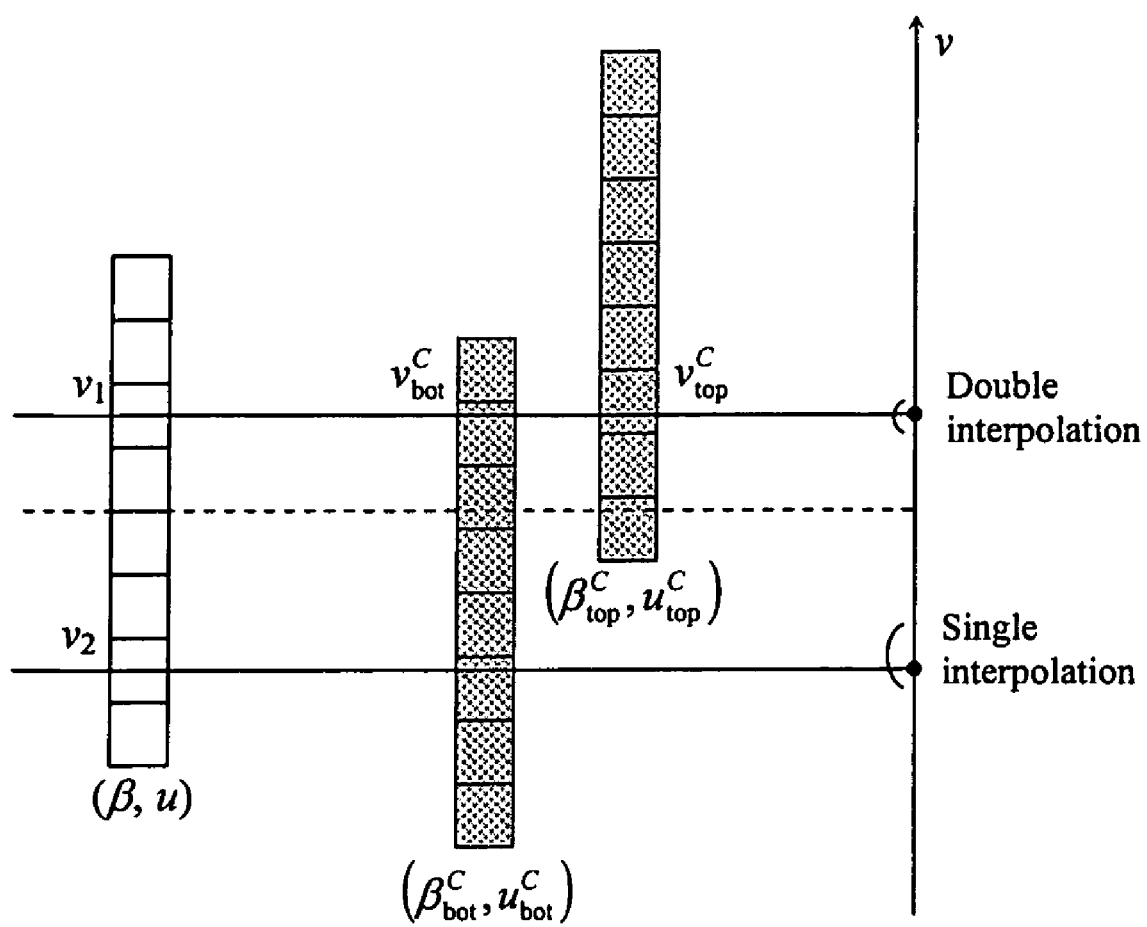
FIG. 13 illustrates nearest linear interpolation, including single and double interpolation.

FIG. 13 illustrates possible nearest linear interpolation scenarios. Once the v-coordinates of the complementary projections are known (say, after using the detector-specific equations previously derived) and the complementary data are lined up along the v-axis, the truncated data can be restored by using the closest complementary data from a complementary projection (or both, whenever available). This can be accomplished since $u_{top}{}^C = u_{bot}{}^C$. This idea can be applied to both single and double interpolation.

Figure 14:
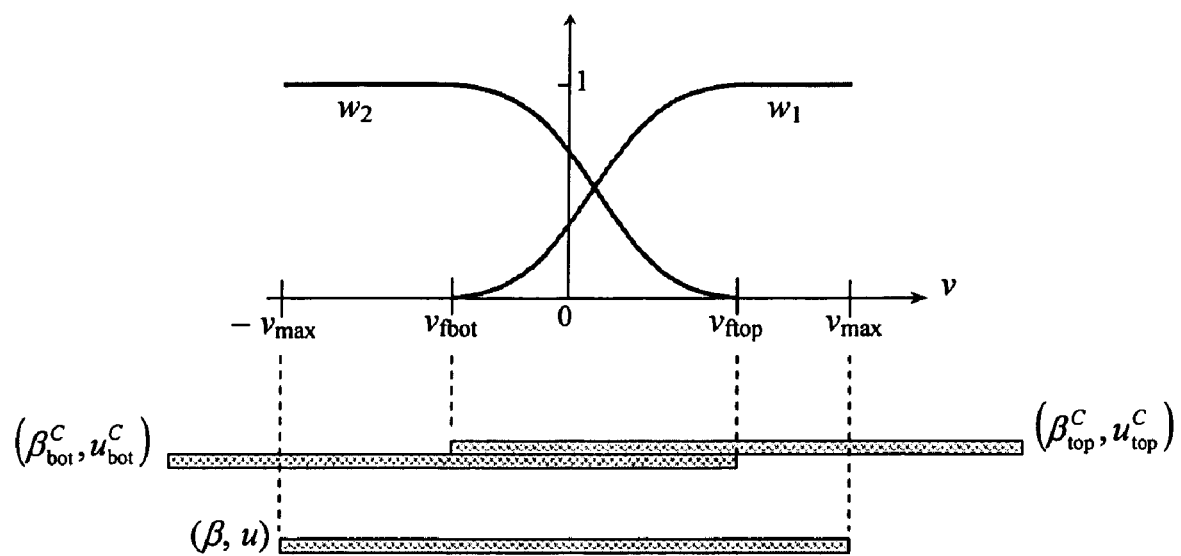
FIG. 14 illustrates the v-feathering process.

FIG. 14 illustrates v-feathering, which can be applied to independently interpolated complementary projections. To do this, of course, both complementary projections must be available. More precisely, v-feathering consists of defining weights $w_1 = 3x^2 - 2x^3$ and $w_2 = 1 - w_1$, where $$x = \frac{v - v_{fbot}}{v_{ftop} - v_{fbot}}$$

and $v_{fbot} \leq v \leq v_{ftop}$, and determining the complementary data using a linear combination. That is, $\underline{PD}(\beta_{top}{}^C, u_{top}{}^C, v_{top}{}^C, \beta_{bot}{}^C, u_{bot}{}^C, v_{bot}{}^C) = w_1 \underline{PD}(\beta_{top}{}^C, u_{top}{}^C, v_{top}{}^C) + w_2 \underline{PD}(\beta_{bot}{}^C, u_{bot}{}^C, v_{bot}{}^C)$. When complementary projections overlap, the $v_{fbot}$ and $v_{ftop}$ parameters illustrated in FIG. 14 are given by $v_{fbot} = 2v_{bot} + v_{max}$ and $v_{ftop} = 2v_{top} - v_{max}$. Naturally, a variety of similar approaches could be entertained while remaining within the scope of the invention.

Figure 15:
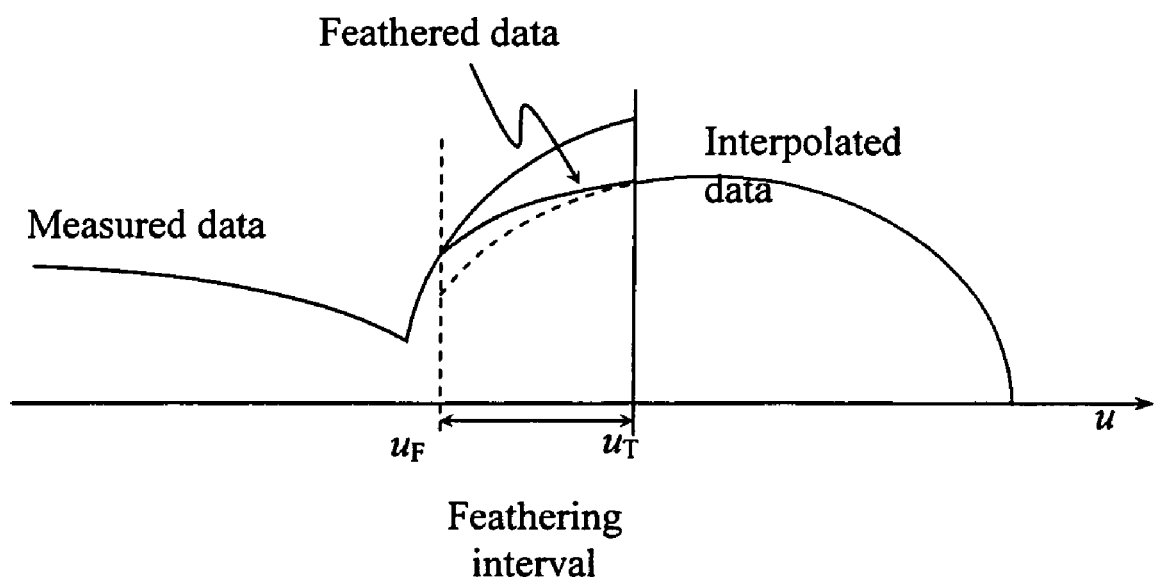
FIG. 15 illustrates feathering between restored and measured data.

FIG. 15 illustrates restoration feathering. The integration of restored data with originally un-truncated data can further be feathered to attenuate the abrupt transition that can arise near the intersection of restored and originally un-truncated data. One possible approach consists of extending the range of data interpolation beyond the truncated/un-truncated boundary along a feathering interval $[u_T, u_F]$, as illustrated in FIG. 15.

To extend the range of data interpolation beyond the truncated/un-truncated boundary along the feathering interval, one can define a weight parameter $w_u = 3x^2 - 2x^3$, where $x = (u_T - u)/(u_T - u_F)$. Using this, the restored data can then be computed as $PD(\beta, u, v) = PD^C(\beta, u, v) w_u + PD'(\beta, u, v)(1 - w_u)$, where $PD'(\beta, u, v)$ denotes projection data that was obtained, but which is to be replaced through feathering with complementary data because it was located in the feathering interval.

Thus far, means to determine complementary projection coordinates have been derived, means to interpolate and feather the complementary data have been proposed, and a means to feather the restored data with the originally available data has also been suggested. Now, these will be put together as the general data restoration process is described.

Let $\underline{PD}(\beta_{top}{}^C, u_{top}{}^C, v_{top}{}^C)$ denote data interpolated from one complementary projection and let $\underline{PD}((\beta_{top}{}^C, u_{top}{}^C, v_{top}{}^C), (\beta_{bot}{}^C, u_{bot}{}^C, v_{bot}{}^C))$ denote data interpolated from two complementary projections.

Figure 16:
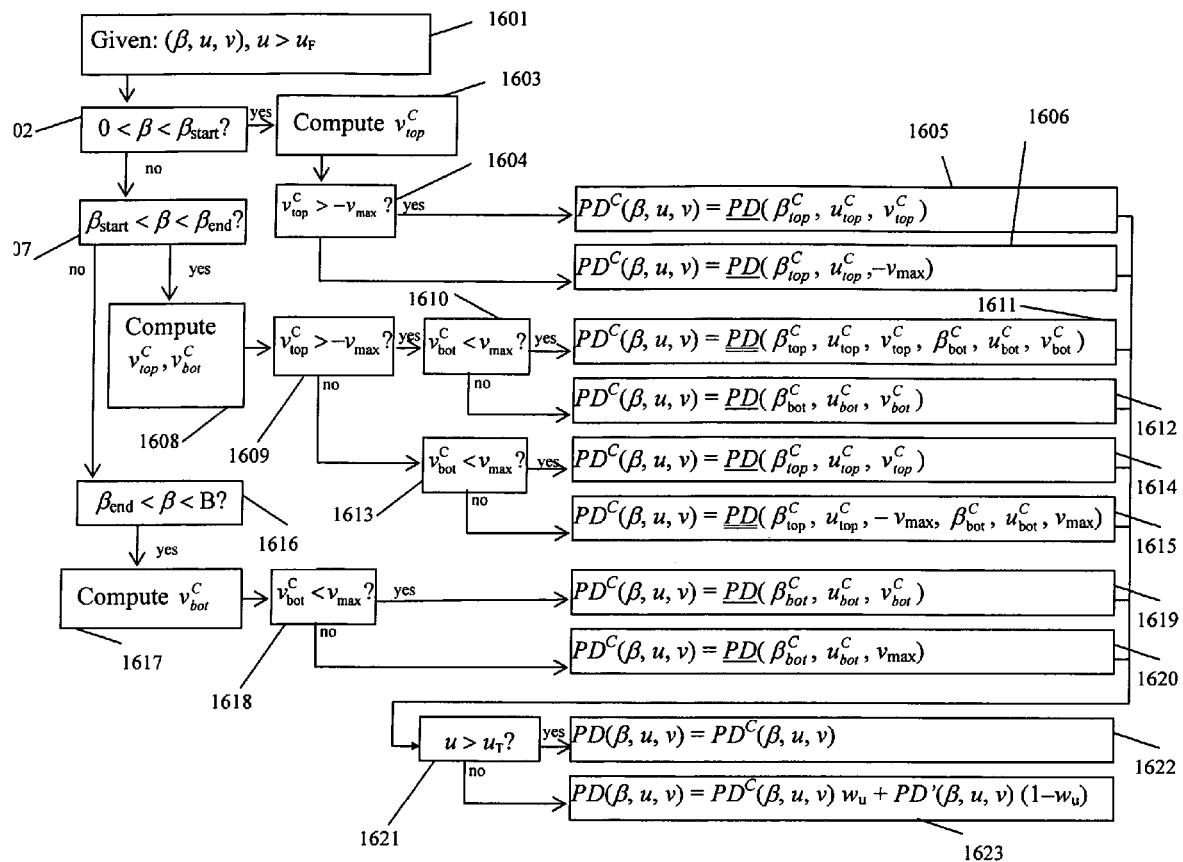
FIG. 16 illustrates the a flowchart describing an embodiment of the present invention.

FIG. 16 displays schematically the process of restoring truncated data. Note that $v_{top}{}^C > v_{max}$, $v_{bot}{}^C > -v_{max}$, and $-u_{max} \leq u_{bot}{}^C$, $u_{top}{}^C \leq -u_{max}$ for all rays $(\beta, u, v)$.

In step 1601, a ray $(\beta, u, v)$ for which $PD(\beta, u, v)$ is sought to be restored is considered. The ray is such that $u > u_F$ since restoration extends into the feathering interval to ultimately yield smoother results. The restoration method considers all cases of complementary projection availability.

In step 1602, it is determined whether $0 < \beta < \beta_{start} = \pi - 2\gamma$. If that is the case, then there can be only one complementary projection $(\beta_{top}{}^C, u_{top}{}^C, v_{top}{}^C)$, step 1603 computes $v_{top}{}^C$, and step 1604 checks whether $v_{top}{}^C > -v_{max}$. If so, then the projection falls on the detector and the truncated data is restored in step 1605 using $PD^C(\beta, u, v) = \underline{PD}(\beta_{top}{}^C, u_{top}{}^C, v_{top}{}^C)$. If not, then the projection falls outside the detector and extrapolation is necessary. Should extrapolation be necessary, the replication of boundary values, is used in step 1606, i.e., $PD^C(\beta, u, v) = \underline{PD}(\beta_{top}{}^C, u_{top}{}^C, -v_{max})$. This is perhaps the simplest and most stable extrapolation method.

In step 1607, it is determined whether $\pi - 2\gamma = \beta_{start} \leq \beta \leq \beta_{end} = B - \pi - 2\gamma$. If that is the case, then there are potentially two complementary projections available, $(\beta_{top}{}^C, u_{top}{}^C, v_{top}{}^C)$ and $(\beta_{bot}{}^C, u_{bot}{}^C, v_{bot}{}^C)$, and step 1608 computes $v_{top}{}^C$ and $v_{bot}{}^C$.

In step 1609, it is determined whether $v_{top}{}^C > -v_{max}$. If so, step 1610 checks whether $v_{bot}{}^C < v_{max}$. If the answer is positive, then both projections falls on the detector and double interpolation is used in step 1611, i.e., $PD^C(\beta, u, v) = \underline{PD}(\beta_{top}{}^C, u_{top}{}^C, v_{top}{}^C, \beta_{bot}{}^C, u_{bot}{}^C, v_{bot}{}^C)$; if the answer is negative, then only the top complementary projection falls on the detector and the truncated data is restored by single interpolation in step 1612 using $PD^C(\beta, u, v) = \underline{PD}(\beta_{top}{}^C, u_{top}{}^C, v_{top}{}^C)$. If it is not the case that $v_{top}{}^C > -v_{max}$, then step 1613 checks whether $v_{bot}{}^C < v_{max}$. If the answer is positive, then only the bottom complementary projection falls on the detector and the truncated data is restored using single interpolation in step 1614, that is, $PD^C(\beta, u, v) = \underline{PD}(\beta_{bot}{}^C, u_{bot}{}^C, v_{bot}{}^C)$; if the answer is negative, then neither complementary projection falls on the detector and extrapolation is used in step 1615: $PD^C(\beta, u, v) = \underline{PD}(\beta_{top}{}^C, u_{top}{}^C, -v_{max}, \beta_{bot}{}^C, u_{bot}{}^C, v_{max})$.

In step 1616, it is determined whether $B - \pi - 2\gamma = \beta_{end} < \beta < B$. If that is the case, then there can only be one complementary projection, $(\beta_{bot}{}^C, u_{bot}{}^C, v_{bot}{}^C)$, step 1617 computes $v_{bot}{}^C$ and step 1618 checks whether $v_{bot}{}^C < v_{max}$. If so, then the projection falls on the detector and the truncated projection data is restored by single interpolation in step 1619 as $PD^C(\beta u, v) = \underline{PD}(\beta_{bot}{}^C, u_{bot}{}^C, v_{bot}{}^C)$. If not, then the projection falls outside the detector and extrapolation is used in step 1620, i.e., $PD^C(\beta, u, v) = \underline{PD}(\beta_{bot}{}^C, u_{max}, v_{bot}{}^C)$.

The method of the present invention therefore obtains the complementary data by extrapolation when complementary projections are not available and by single or double interpolation when one or both complementary projections are available. Subsequently, in step 1621 it is determined whether $u > u_T$. If that is the case, then in step 1622 the projection data is simply deemed to be the complementary data previously obtained (in one of steps 1605, 1606, 1611, 1612, 1614, 1615, 1619, or 1620). That is, $PD(\beta, u, v) = PD^C(\beta, u, v)$. If that is not the case, then feathering between the complementary data obtained and the originally un-truncated data is performed in step 1623. That is, $PD(\beta, u, v) = PD^C(\beta u, v) w_u + PD'(\beta, u, v)(1 - w_u)$.

Figure 17:
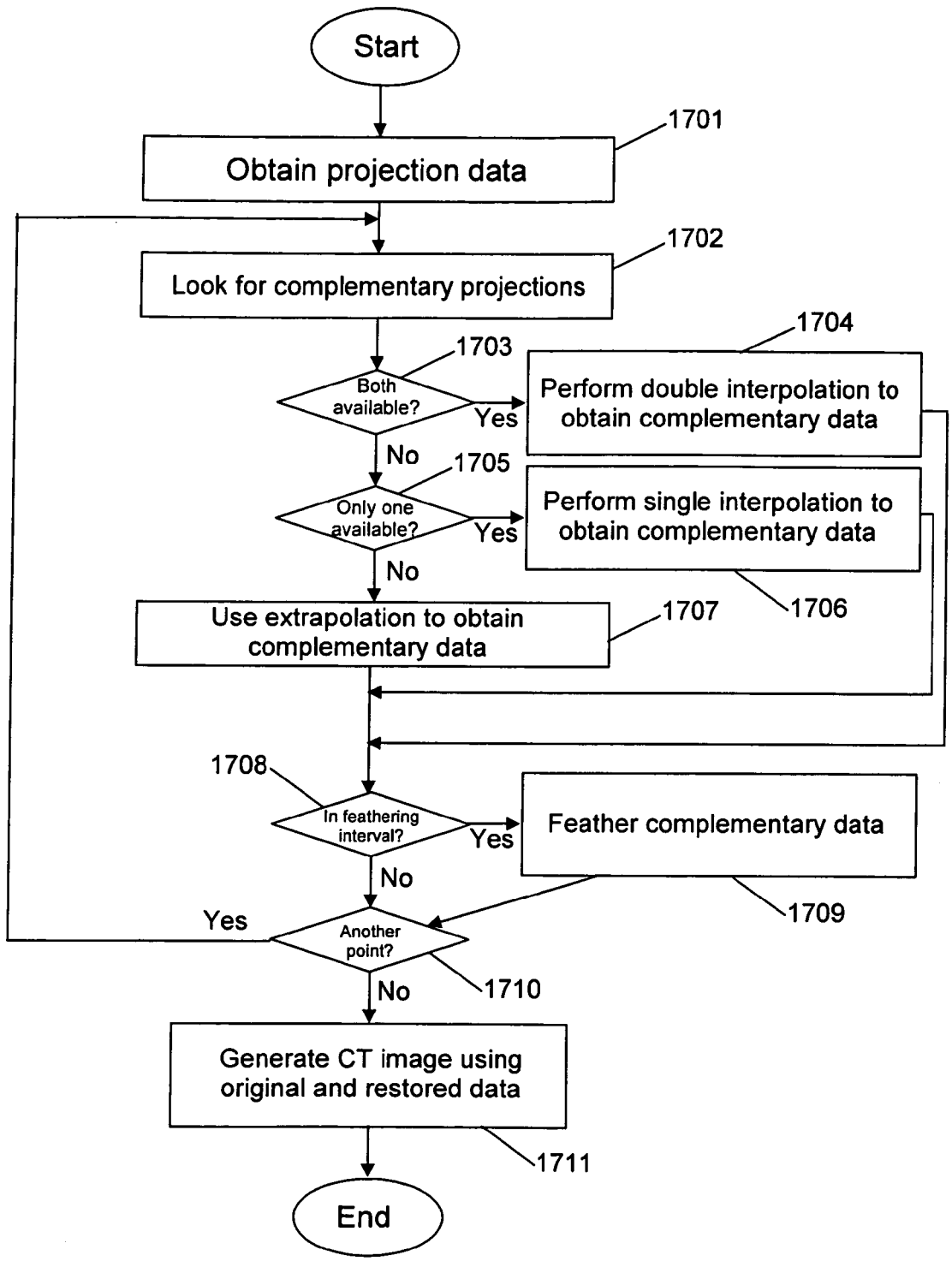
FIG. 17 illustrates a method for restoring truncated projection data values.

FIG. 17 illustrates a flowchart of an embodiment of the present invention. In step 1701, redundant projection data are obtained to determine a projection data value. Complementary projections are then sought in step 1702.

In step 1703, a determination is made whether two projections are available. If so, double interpolation is used to obtain complementary data in step 1704. Otherwise, a determination is made in step 1705 whether one projection is available. If so, single interpolation is used to obtain complementary data in step 1706. Otherwise, no projections are available and extrapolation is used in step 1707.

In step 1708, a determination is made whether the projection data value sought to be determined is located within a feathering interval. If so, then feathering is performed on the newly obtained and originally available projection data values in step 1709. Otherwise, in step, 1710, a determination is made whether to repeat the whole process for a new location. If the answer is negative, then the data have been restored and a CT image can be obtained using any reconstruction algorithm in step 1711.

Since reconstruction algorithms usually process projections one at a time, it may be computationally difficult to store all the necessary projections to restore the entirety of the truncated data. For instance, if the data consist of $N_P$ projections per rotation, then the complementary projection range for a single direct ray is $N_A = N_P \Delta\gamma/\pi$, so that for $N_p = 1000$ and $\Delta\gamma = \pi/10$ it is necessary to store $N_A = 100$ projections for each truncated projection. Such a requirement might be difficult to meet for many systems. It is possible, however, to reduce the requirement on the number of stored projections. Naturally, this may result is lesser image quality.

An embodiment of the present invention addresses this concern by storing 2K projections, where $K=1,2,\ldots,N_A$. The truncation interval $\Delta\gamma$ can then be partitioned into K parts with angles $\gamma_k = \gamma_T + k\Delta\gamma/K + \gamma_{offset}$, $k=0,1,\ldots,K-1$. (The parameter $\gamma_{offset}$ is given for flexibility in choosing $\gamma_k$.)

Now, choose K top complementary projections $\beta_{top}^C(k) = \beta + \pi + 2\gamma_k$ and K bottom complementary projections $\beta_{bot}^C(k) = \beta - \pi + 2\gamma_k$. For each discrete value of v corresponding to a projection β the K complementary data points $\underline{PD}(\beta_{top}^C(k), u(\gamma_k), v)$ and $\underline{PD}(\beta_{bot}^C(k), u(\gamma_k), v)$ can be interpolated from K complementary projections.

The u-grid points can then be interpolated from these K points. For example, the data could be restored only every 10th point with interpolation in between. Linear interpolation is preferred, but nearest neighbor or non-linear interpolation could also be used.

Restoring data every second or third u-grid point does not necessary lead to two or three times fewer complementary projections that need to be stored. This is the case since the u-grid is usually denser than the β-grid. In the example above, supposing that $\gamma_{max} = \pi/6$ corresponds to 500 samples, the truncation range $\Delta_\gamma$ has 300 u-samples. Each complementary view therefore contributes to the restoration of at least 3 u-samples (and possibly more, because of linear interpolation). Consequently, restoring data every fourth or fifth u-sample, at least, is necessary to reduce the number of stored projections.

When only a small K can be afforded, it is better to restore data at every u-sample $\underline{PD}(\beta_{top}^C(k), u, v)$ using only complementary projections $\beta_{top}^C(k)$ and $\beta_{bot}^C(k)$. That is, using only angles $\beta_{top}^C(k) = \beta + \pi + 2\gamma_k$, $\gamma_k - \Delta\gamma/2K \leq \gamma \leq \gamma_k + \Delta\gamma/2K$, for the top projections and angles $\beta_{bot}^C(k) = \beta - \pi + 2\gamma_k$, $\gamma_k - \Delta\gamma/2K \leq \gamma \leq \gamma_k + \Delta\gamma/2K$, for the bottom projections.

As a special case, one complementary projection above and one below are used to restore truncated data. This approach can be used when only general information about reconstructed object needs to be evaluated, such as object boundary position. There is then a single angle, $\gamma_0 = \gamma_T + \Delta\gamma/2 + \gamma_{offset}$, $-\Delta\gamma/2 \leq \gamma_{offset} \leq \Delta\gamma/2$, and the complementary projections correspond to $\beta_{top}^C = \beta + \pi + 2\gamma_0$ and $\beta_{bot}^C = \beta - \pi + 2\gamma_0$ for all truncated u-samples. The two complementary projections are simply blended together to obtain direct truncated projection. Other possible approaches could be considered. For example, only data related to edge position could be extracted and nonlinear extrapolation used thereupon from the measured samples to the recovered edge of the object.

A mismatch on the edge between measured and interpolated data can arise when $\gamma_{offset} \neq -\Delta\gamma/2$, i.e., when $\gamma_0 > \gamma_T$. This will result in strong artifacts within reconstructed images. To avoid this mismatch, the data between $\gamma_T$ and $\gamma_0$ can be smoothly feathered.

The can be more than one complementary projection available along both helical directions for slow helical pitches. The complementary projection angles can then generally be expressed as $\beta_n^C = \beta + n\pi + 2\gamma$, $n = \pm 1, 2, \ldots$ In this context, using cylindrical coordinates, the projection corresponding to β has N common rays with N complementary projections for each value of γ: $g(\beta, \gamma, z_n) = g(\beta_n^C, -\gamma, -z_n)$, $n = \pm 1, 2, \ldots$ It follows that $$z_n = \frac{H}{4\pi} \frac{n\pi + 2\gamma}{\cos\gamma},$$

and, therefore, that for each direct ray (β,γ,z) there are N complementary rays given by $$(\beta_{top}^C, \gamma_{top}^C, z_{top}^C) = \left(\beta + n\pi + 2\gamma, -\gamma, z - \frac{H}{2\pi}\frac{n\pi + 2\gamma}{\cos\gamma}\right).$$

Figure 18:
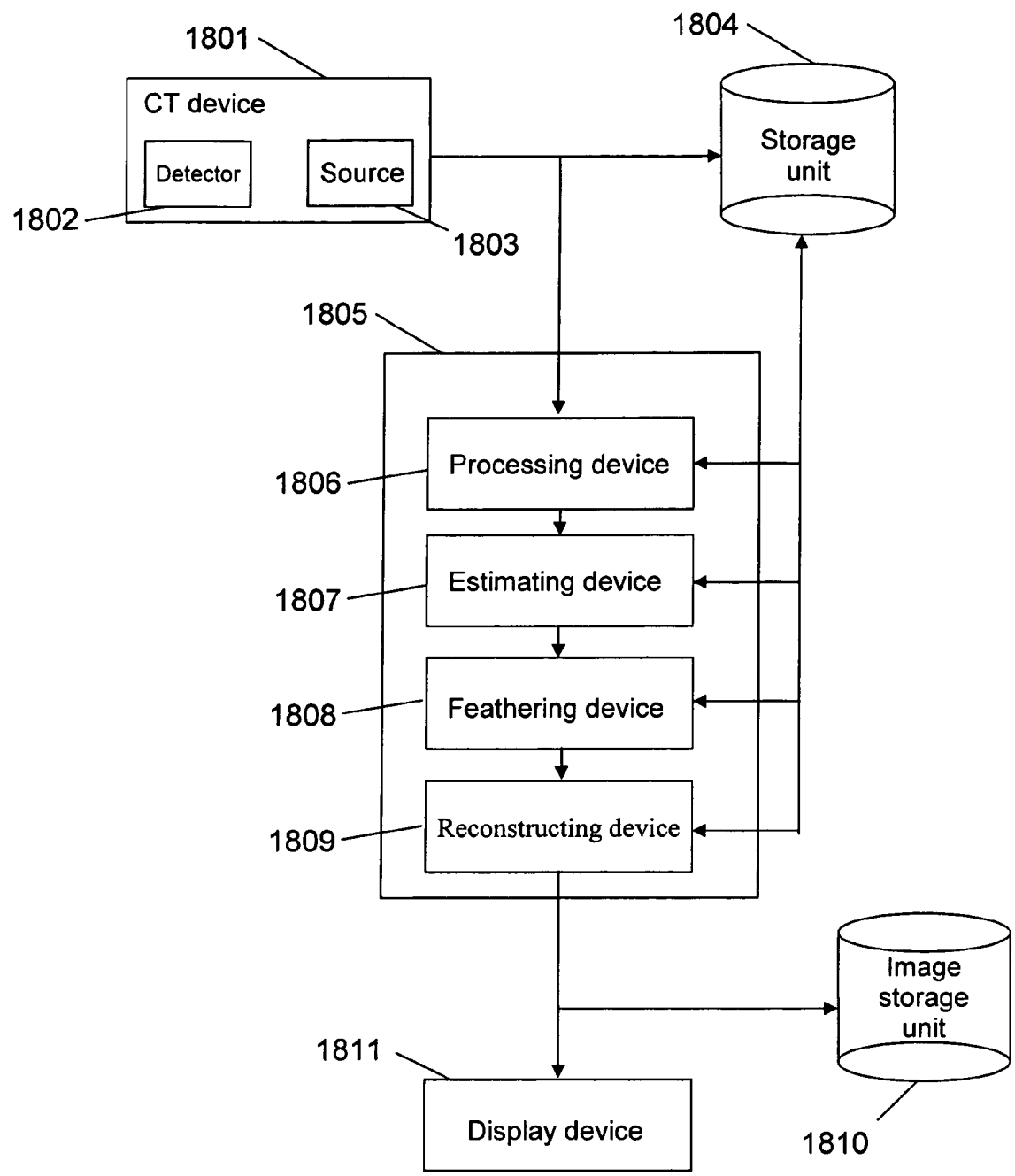
FIG. 18 illustrates a system for carrying out the method illustrated in FIG. 17.

FIG. 18 illustrates a system for carrying out embodiments of the present invention. A CT device 1801 comprising a ray detector 1802 and a ray source 1803 are used to acquire CT data. The data can be stored using a storage unit 1804. The data can be processed by a computing unit 1805 comprising a processing device 1806, which identifies suitable data elements that can be used to determine complementary projection data values, an estimating device 1807, which can estimate projection data values based on suitable redundant data, a feathering device 1808, which can smooth the boundary between newly generated and previously available data, and a reconstructing device 1809, which can reconstruct a scanned object from the acquired data using at least one weight to compensate for the unavailability of the projection data. The system further comprises an image storing unit 1810 to store images obtained using the data and computing unit and a display device 1811 to display those same images. Additionally, the processing device 1806 includes a complementary processor (not shown) configured to determine complementary projection angles for a given source angle.

All embodiments of the present invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art. In particular, the computer housing may house a motherboard that contains a CPU, memory (e.g., DRAM, ROM, EPROM, EEPROM, SRAM, SDRAM, and Flash RAM), and other optional special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

Examples of computer readable media associated with the present invention include compact discs, hard disks, floppy disks, tape, magneto-optical disks, PROMs (e.g., EPROM, EEPROM, Flash EPROM), DRAM, SRAM, SDRAM, etc. Stored on any one or on a combination of these computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g., computer code devices) which when executed by a computer causes the computer to perform the method of the present invention. The computer code devices of the present invention may be any interpretable or executable code mechanism, including but not limited to, scripts, interpreters, dynamic link libraries, Java classes, and complete executable programs. Moreover, parts of the processing of the present invention may be distributed (e.g., between (1) multiple CPUs or (2) at least one CPU and at least one configurable logic device) for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

The source of projection data to the present invention may be any appropriate data acquisition device such as an X-ray machine or CT apparatus. Further, the acquired data may be digitized if not already in digital form. Alternatively, the source of data being obtained and processed may be a memory storing data produced by an image acquisition device, and the memory may be local or remote, in which case a data communication network, such as PACS (Picture Archiving Computer System), may be used to access the image data for processing according to the present invention. This invention can be a part of a CT apparatus.

Alternatively, in an embodiment of the present invention, truncated data compensation can be implemented by appropriate weighting of the asymmetric existing data during image reconstruction.

Numerous modifications and variations of the present invention are possible in light of the above teachings. It is therefore to be understood that within the scope of the appended claims, the invention may be practiced otherwise than as specifically described.

The invention claimed is:

1. A method for compensating for the unavailability of projection data of a scanned object at a selected point, the selected point located outside a detection range of a detector, comprising:

obtaining helical cone-beam projection data of the scanned object;

compensating for the unavailability of the projection data at said selected point based on the obtained projection data and coordinates of the selected point relative to the detector to obtain at least one weight, wherein the compensating step comprises performing extrapolation based on available complementary projection data to generate complementary projection data for a middle part of a direct projection when no complementary projection data is available for the middle part of the direct projection due to a large helical pitch;

reconstructing the image of the scanned object based on the obtained projection data and the obtained at least one weight; and displaying the reconstructed image.

2. The method of claim 1, wherein said compensating step comprises:

determining at least one complementary projection angle and coordinates of at least one complementary point based on a source projection angle and the coordinates of the selected point relative to the detector; and calculating the at least one weight corresponding to the at least one complementary point, said at least one weight being used to compensate for the unavailability of the projection data of the scanned object at the selected point in reconstructing an image of the scanned object.

3. The method claim 1, wherein said compensating step comprises:

determining at least one complementary projection angle and coordinates of at least one complementary point based on a source projection angle and the coordinates of the selected point relative to the detector; and estimating the projection data value at the selected point based on the acquired projection data, the at least one complementary projection angle, and the coordinates of the at least one complementary point.

4. The method of claim 3, further comprising:

repeating said determining and estimating steps for a plurality of selected points located outside the detection range of the detector to estimate a corresponding plurality of projection data values.

5. The method of claim 3, wherein the obtaining step comprises:

obtaining computed tomography (CT) projection data of the scanned object.

6. The method of claim 5, wherein the determining step comprises:

determining the at least one complementary point in detector-free coordinates applicable to any detector geometry, including one of cylindrical, equi-angular, flat equi-spaced, non-equi-spaced, spherical, tilted, rotated, and PI-masked.

7. The method of claim 5, wherein the obtaining step comprises obtaining the projection data of the scanned object using an equi-angular detector; and the determining step comprises determining the at least one complementary projection angle and the coordinates of the at least one complementary point as, respectively, $$\left(\beta \pm \pi + 2\gamma, -u, v \mp \frac{H}{2\pi}\frac{\pi \pm 2u/R}{\cos(u/R)}\right),$$

wherein β is the source projection angle, γ is a fan angle, u and v are the coordinates of the projection data value, R is a helical radius, and H is a helical pitch.

8. The method of claim 5, wherein
the obtaining step comprises obtaining the projection data of the scanned object using an equi-angular detector; and
the determining step comprises determining the at least one complementary projection angle and the coordinates of the at least one complementary point as, respectively, $$\left(\beta \pm \pi + 2\gamma, -u, v \mp \frac{H}{2\pi}\frac{n\pi \pm 2u/R}{\cos(u/R)}\right),$$

wherein β is the source projection angle, γ is a fan angle, n is an integer such that n=1, ..., N, N is an integer number of helical turns for which data are acquired, u and v are the coordinates of the projection data value, R is a helical radius, and H is a helical pitch.

9. The method of claim 5, wherein
the obtaining step comprises obtaining the projection data of the scanned object using an equi-spaced flat detector; and
the determining step comprises determining the at least one complementary projection angle and the coordinates of the at least one complementary point as, respectively, $$\left(\beta \pm \pi + 2\gamma, -u, v \mp \frac{\pi \pm 2\tan^{-1}(u/R)}{2\pi}\frac{H(u^2+R^2)}{R^2}\right),$$

wherein β is the source projection angle, γ is a fan angle, u and v are the coordinates of the projection data value, R is a helical radius, and H is a helical pitch.

10. The method of claim 5, wherein
the obtaining step comprises obtaining the projection data of the scanned object using an equi-spaced flat detector; and
the determining step comprises determining the at least one complementary projection angle and the coordinates of the at least one complementary point as, respectively, $$\left(\beta \pm \pi + 2\gamma, -u, v \mp \frac{n\pi \pm 2\tan^{-1}(u/R)}{2\pi}\frac{H(u^2+R^2)}{R^2}\right),$$

wherein β is the source projection angle, γ is a fan angle, n=1, ..., N, N is an integer number of helical turns for which data are acquired, u and v are the coordinates of the projection data value, R is a helical radius, and H is a helical pitch.

11. The method of claim 5, wherein the determining step comprises:
determining the at least one complementary projection angle to be at least one of the projection angles $\beta+n\pi+2\gamma_0$ and $\beta-n\pi+2\gamma_0$, wherein β is the source projection angle, n=1,2,..., N, N is an integer number of helical turns for which data are acquired, and $\gamma_0$ is a parameter that depends on a size of the scanned object and an angular range of the detector.

12. The method of claim 5, wherein the determining step comprises:
determining the at least one complementary projection angle to be at least one of projection angles $\beta+n\pi+2\gamma_k$, n=1, ..., N, k=1, ..., K and projection angles $\beta-n\pi+2\gamma_k$, n=1, ..., N, k=1, ..., K, wherein k and n are integers, N is an integer number of helical turns for which data are acquired, K is a predetermined integer, and $\gamma_k$, k=1, ..., K are parameters that depend on a density of the projection data, a size of the scanned object, and an angular range of the detector.

13. The method of claim 5, wherein the determining step comprises:
determining the at least one complementary angle along one helical direction.

14. The method of claim 5, wherein the determining step comprises:
determining the at least one complementary angle along both helical directions.

15. The method of claim 5, wherein the determining step comprises:
determining the at least one complementary angle along both helical directions, but within a predetermined numbers of helical turns.

16. The method of claim 5, wherein
the determining step comprises determining two complementary projection angles and coordinates of two complementary points corresponding to the two complementary projection angles; and
the estimating step comprises estimating the projection data value based on the two complementary projection angles and the coordinates of two complementary points.

17. The method of claim 5, wherein
the determining step comprises determining two complementary projection angles and coordinates of two complementary points corresponding to the two complementary projection angles; and
the estimating step comprises estimating the projection data value by independently using one of nearest-neighbor, linear, and non-linear interpolation for each of the two complementary points to obtain two sets of interpolated coordinates.

18. The method of claim 17, wherein the estimating step comprises:
combining projection data at each of the two sets of interpolated coordinates to obtain the projection data value.

19. The method of claim 18, wherein the combining step comprises:
linearly combining the projection data at each of the two sets of interpolated coordinates using weights $w_1=3x^2-2x^3$ and $w_2=1-w_1$, wherein $x=(v-v_{fbot})/(v_{ftop}-v_{fbot})$, $v_{fbot} \leq v \leq v_{ftop}$, and $v_{ftop}$ and $v_{fbot}$ are predetermined parameters.

20. The method of claim 3, wherein the determining step comprises:
determining the at least one complementary projection angle to be one of projection angle $\beta+\pi+2\gamma_0$ and projection angle $\beta-\pi+2\gamma_0$, wherein β is the source projection angle and $\gamma_0$ is a parameter that depends on a size of the scanned object and an angular range of the detector.

21. The method of claim 3, wherein the determining step comprises:
determining the at least one complementary projection angle to be projection angles $\beta+\pi+2\gamma_0$ and $\beta-\pi+2\gamma_0$, wherein β is the source projection angle and $\gamma_0$ is a parameter that depends on a size of the scanned object and an angular range of the detector.

22. The method of claim 3, wherein the determining step comprises:
   determining the at least one complementary projection angle to be at least one of projection angles $\beta+\pi+2\gamma_k$, k=1, ..., K or at least one of projection angles $\beta-\pi+2\gamma_k$, k=1, ..., K, wherein k is an integer, K is a predetermined integer, and $\gamma_k$, k=1, ..., K are parameters that depend on a density of the projection data, a size of the scanned object, and an angular range of the detector.

23. The method of claim 3, wherein the determining step comprises:
   determining the at least one complementary projection angle to be at least one of projection angles $\beta+\pi+2\gamma_k$, k=1, ..., K and projection angles $\beta-\pi+2\gamma_k$, k=1, ..., K, wherein k is an integer, K is a predetermined integer, and $\gamma_k$, k=1, ..., K are parameters that depend on a density of the projection data, a size of the scanned object, and an angular range of the detector.

24. The method of claim 3, wherein
   the determining step comprises determining one complementary projection angle and coordinates of one complementary point corresponding to the one complementary projection angle; and
   the estimating step comprises estimating the projection data value using one of nearest-neighbor, linear, and non-linear interpolation based on the coordinates of the one complementary point.

25. The method of claim 3, further comprising:
   selecting a feathering point within a predetermined feathering region of the detector;
   determining at least one feathering complementary angle and coordinates of at least one feathering complementary point based on a feathering source projection angle and coordinates of the feathering point relative to the detector;
   estimating the projection data value at the feathering point based on the obtained projection data, the at least one feathering complementary projection angle, and the coordinates of the at least one feathering complementary point; and
   linearly combining the estimated projection data value at the feathering point with the obtained projection data at the feathering point using weights $w_u=3x^2-2x^3$ and $1-w_u$, respectively, wherein $x=(u_T-u)/(u_T-u_F)$, and $u_F$ and $u_T$ are parameters that define the predetermined region of the detector.

26. A computer program product storing instructions for execution on a computer system, which when executed by the computer system, causes the computer system to compensate for the unavailability of projection data of a scanned object at a selected point, the selected point located outside a detection range of a detector, by performing the steps of:
   obtaining helical cone-beam projection data of the scanned object;
   compensating for the unavailability of the projection data at said selected point based on the obtained projection data and coordinates of the selected point relative to the detector to obtain at least one weight, wherein the compensating step comprises performing extrapolation based on available complementary projection data to generate complementary projection data for a middle part of a direct projection when no complementary projection data is available for the middle part of the direct projection due to a large helical pitch;
   reconstructing the image of the scanned object based on the obtained projection data and the obtained at least one weight; and
   displaying the reconstructed image.

27. A computed tomography (CT) system to compensate for the unavailability of projection data of a scanned object at a selected point, the selected point located outside a detection range of a detector, comprising:
   an X-ray source configured to project X-rays at a scanned object;
   an asymmetric CT detector configured to detect said X-rays and to generate helical cone-beam CT projection data of the scanned object;
   a compensating processor configured to compensate for the unavailability of the projection data at said selected point based on the generated projection data and coordinates of the selected point relative to the CT detector,
   wherein the compensating processor is configured to perform extrapolation based on available complementary projection to generate complementary projection data for a middle part of a direct projection when no complementary projection data is available for the middle part of the direct projection due to a large helical pitch.

28. The CT system of claim 27, wherein said compensating processor comprises:
   a complementary processor configured to determine at least one complementary projection angle and coordinates of at least one complementary point based on a source projection angle and the coordinates of the selected point relative to the detector; and
   a weighting device configured to calculate at least one weight corresponding to the at least one complementary point, said at least one weight being used to compensate for the unavailability of the projection data of the scanned object at the selected point in reconstructing a CT image of the scanned object.

29. The CT system of claim 28, further comprising:
   a CT reconstruction device configure to reconstruct the CT image of the scanned object based on the obtained projection data, the at least one complementary point, and the calculated at least one weight.

30. The CT system of claim 27, wherein said compensating processor comprises:
   a complementary processor configured to determine at least one complementary projection angle and coordinates of at least one complementary point based on a source projection angle and the coordinates of the selected point relative to the detector; and
   an estimating device configured to compensate for the unavailability of the projection data of the scanned object at the selected point by estimating the projection data value at the selected point based on the acquired projection data, the at least one complementary projection angle, and the coordinates of the at least one complementary point.

31. The CT system of claim 30, wherein
   the CT detector comprises an equi-angular detector; and
   the complementary processor is configured to determine the at least one complementary projection angle and the coordinates of the at least one complementary point as, respectively, $$\left(\beta \pm \pi + 2\gamma, -u, v \mp \frac{H}{2\pi}\frac{\pi \pm 2u/R}{\cos(u/R)}\right),$$

wherein $\beta$ is the source projection angle, $\gamma$ is a fan angle, u and v are the coordinates of the projection data value, R is a helical radius, and H is a helical pitch.

32. The CT system of claim 30, wherein
the CT detector comprises an equi-angular detector; and
the complementary processor is configured to determine the at least one complementary projection angle and the coordinates of the at least one complementary point as, respectively, $$\left(\beta \pm \pi + 2\gamma, -u, v \mp \frac{H}{2\pi}\frac{n\pi \pm 2u/R}{\cos(u/R)}\right),$$

wherein $\beta$ is the source projection angle, $\gamma$ is a fan angle, n is an integer such that $n=1, \ldots, N$, N is an integer number of helical turns for which data are acquired, u and v are the coordinates of the projection data value, R is a helical radius, and H is a helical pitch.

33. The CT system of claim 30, wherein
the CT detector comprises an equi-spaced flat detector; and
the complementary processor is configured to determine the at least one complementary projection angle and the coordinates of the at least one complementary point as, respectively, $$\left(\beta \pm \pi + 2\gamma, -u, v \mp \frac{\pi \pm 2\tan^{-1}(u/R)}{2\pi}\frac{H(u^2+R^2)}{R^2}\right),$$

wherein $\beta$ is the source projection angle, $\gamma$ is a fan angle, u and v are the coordinates of the projection data value, R is a helical radius, and H is a helical pitch.

34. The CT system of claim 30, wherein
the CT detector comprises an equi-spaced flat detector; and
the complementary processor is configured to determine the at least one complementary projection angle and the coordinates of the at least one complementary point as, respectively, $$\left(\beta \pm \pi + 2\gamma, -u, v \mp \frac{n\pi \pm 2\tan^{-1}(u/R)}{2\pi}\frac{H(u^2+R^2)}{R^2}\right),$$

wherein $\beta$ is the source projection angle, $\gamma$ is a fan angle, $n=1, \ldots, N$, N is an integer number of helical turns for which data are acquired, u and v are the coordinates of the projection data value, R is a helical radius, and H is a helical pitch.

35. The CT system of claim 32, wherein the complementary processor is configured to determine the at least one complementary projection angle to be one of projection angle $\beta+\pi+2\gamma_0$ and projection angle $\beta-\pi+2\gamma_0$, wherein $\beta$ is the source projection angle and $\gamma_0$ is a parameter that depends on a size of the scanned object and an angular range of the detector.

36. The CT system of claim 30, wherein the complementary processor is configured to determine the at least one complementary projection angle to be projection angles $\beta+\pi+2\gamma_0$ and $\beta-\pi+2\gamma_0$, wherein $\beta$ is the source projection angle and $\gamma_0$ is a parameter that depends on a size of the scanned object and an angular range of the detector.

37. The CT system of claim 30, wherein the complementary processor is configured to determine the at least one complementary projection angle to be at least one of the projection angles $\beta+n\pi+2\gamma_0$ and $\beta-n\pi+2\gamma_0$, wherein $\beta$ is the source projection angle, $n=1,2,\ldots,N$, N is an integer number of helical turns for which data are acquired, and $\gamma_0$ is a parameter that depends on a size of the scanned object and an angular range of the detector.

38. The CT system of claim 30, wherein the complementary processor is configured to determine the at least one complementary projection angle to be at least one of projection angles $\beta+\pi+2\gamma_k$, $k=1,\ldots,K$ or at least one of projection angles $\beta-\pi+2\gamma_k$, $k=1,\ldots,K$, wherein k is an integer, K is a predetermined integer, and $\gamma_k$, $k=1,\ldots,K$ are parameters that depend on a density of the projection data, a size of the scanned object, and an angular range of the detector.

39. The CT system of claim 30, wherein the complementary processor is configured to determine the at least one complementary projection angle to be at least one of projection angles $\beta+\pi+2\gamma_k$, $k=1,\ldots,K$ and projection angles $\beta-\pi+2\gamma_k$, $k=1,\ldots,K$, wherein k is an integer, K is a predetermined integer, and $\gamma_k$, $k=1,\ldots,K$ are parameters that depend on a density of the projection data, a size of the scanned object, and an angular range of the detector.

40. The CT system of claim 30, wherein the complementary processor is configured to determine the at least one complementary projection angle to be at least one of projection angles $\beta+n\pi+2\gamma_k$, $n=1,\ldots,N$, $k=1,\ldots,K$ and projection angles $\beta-n\pi+2\gamma_k$, $n=1,\ldots,N$, $k=1,\ldots,K$, wherein k and n are integers, N is an integer number of helical turns for which data are acquired, K is a predetermined integer, and $\gamma_k$, $k=1,\ldots,K$ are parameters that depend on a density of the projection data, a size of the scanned object, and an angular range of the detector.

41. The CT system of claim 30, wherein the complementary processor is configured to determine the at least one complementary angle along one helical direction.

42. The CT system of claim 30, wherein the complementary processor is configured to determine the at least one complementary angle along both helical directions.

43. The CT system of claim 30, wherein the complementary processor is configured to determine the at least one complementary angle along both helical directions, but within a predetermined numbers of helical turns.

44. The CT system of claim 30, wherein
the complementary processor is configured to determine two complementary projection angles and coordinates of two complementary points corresponding to the two complementary projection angles; and
the estimating device is configured to estimate the projection data value based on the two complementary projection angles and the coordinates of two complementary points.

45. The CT system of claim 30, wherein
the complementary processor is configured to determine one complementary projection angle and coordinates of one complementary point corresponding to the one complementary projection angle; and the estimating device is configured to estimate the projection data value using one of nearest-neighbor, linear, and non-linear interpolation based on the coordinates of the one complementary point.

46. The CT system of claim 30, wherein the complementary processor is configured to determine two complementary projection angles and coordinates of two complementary points corresponding to the two complementary projection angles; and the estimating device is configured to estimate the projection data value by independently using one of nearest-neighbor, linear, and non-linear interpolation for each of the two complementary points to obtain two sets of interpolated coordinates.

47. The CT system of claim 46, wherein the estimating device comprises:

a combining device configured to combine projection data at each of the two sets of interpolated coordinates to obtain the projection data value.

48. The CT system of claim 47, wherein the combining device is configured to linearly combine the projection data at each of the two sets of interpolated coordinates using weights $w_1=3x^2-2x^3$ and $w_2=1-w_1$, wherein $x=(v-v_{fbot})/(v_{ftop}-v_{fbot})$, $v_{fbot} \leq v \leq v_{ftop}$, and $v_{ftop}$ and $v_{fbot}$ are predetermined parameters.

49. The CT system of claim 30, further comprising:

means for selecting a feathering point within a predetermined feathering region of the detector;

a feathering device configured to (1) determine at least one feathering complementary angle and coordinates of at least one feathering complementary point based on a feathering source projection angle and coordinates of the feathering point relative to the detector, (2) estimate the projection data value at the feathering point based on the obtained projection data, the at least one feathering complementary projection angle, and the coordinates of the at least one feathering complementary point, and (3) linearly combine the estimated projection data value at the feathering point with the obtained projection data at the feathering point using weights $w^u=3x^2-2x^3$ and $1-w_u$, respectively, wherein $x=(u_T-u)/(u_T-u_F)$, and $u_F$ and $u_T$ are parameters that define the predetermined region of the detector.

* * * * *